(12) United States Patent
Nunomura et al.

(10) Patent No.: US 7,001,355 B2
(45) Date of Patent: Feb. 21, 2006

(54) SKIN CARE DEVICE

(75) Inventors: Mahito Nunomura, Osaka (JP); Takafumi Oba, Hikone (JP); Yuko Matsumura, Takatsuki (JP); Gen Nonaka, Kobe (JP); Hidekazu Tanaka, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 209 days.

(21) Appl. No.: 10/460,911

(22) Filed: Jun. 13, 2003

(65) Prior Publication Data

US 2004/0010222 A1 Jan. 15, 2004

Related U.S. Application Data

(63) Continuation of application No. PCT/JP03/00455, filed on Jan. 21, 2003.

(30) Foreign Application Priority Data

Jan. 21, 2002 (JP) .............................. 2002-012143

(51) Int. Cl.
*A61B 17/20* (2006.01)
(52) U.S. Cl. ....................................... 604/22
(58) Field of Classification Search ................. 604/20, 604/22, 500, 501, 890.1; 601/2; 606/169–171, 606/128
See application file for complete search history.

(56) References Cited

U.S. PATENT DOCUMENTS

| | | |
|---|---|---|
| 4,372,296 A | 2/1983 | Fahim |
| 4,787,888 A | 11/1988 | Fox |
| 5,267,985 A | 12/1993 | Shimada et al. |
| 5,383,848 A | 1/1995 | Hillman et al. |
| 5,445,611 A | 8/1995 | Eppstein et al. |
| 5,722,397 A | 3/1998 | Eppstein |
| 6,066,123 A | 5/2000 | Li et al. |
| 6,183,426 B1 | 2/2001 | Akisada et al. |
| 6,350,459 B1 | 2/2002 | Suzuki et al. |
| 2001/0041856 A1 | 11/2001 | McDaniel |
| 2002/0055702 A1 | 5/2002 | Atala et al. |

FOREIGN PATENT DOCUMENTS

| | | |
|---|---|---|
| GB | 1577551 | 10/1980 |
| JP | 9-301852 A | 11/1997 |
| JP | 10-287524 A | 10/1998 |
| JP | 10-298028 A | 11/1998 |
| JP | 10-298029 A | 11/1998 |
| JP | 10-338619 A | 12/1998 |

(Continued)

*Primary Examiner*—Manuel Mendez
(74) *Attorney, Agent, or Firm*—Juliet A. Jones; Eileen L. Hughett; John M. Howell

(57) ABSTRACT

Disclosed is a device for penetrating a skin active agent to the human body via the skin by the use of an ultrasound applying apparatus which applies ultrasound to the human body via the skin, comprising: (1) composition comprising: (a) safe and effective amount of the skin active agent; (b) a viscosifying agent that provides the composition a viscosity of from about 1,000 mPas to about 1,000,000 mPas; (c) from about 0.1% to about 30% of a water-soluble humectant; and (d) an aqueous carrier; wherein the composition is substantially free of surfactants; and (2) the ultrasound applying apparatus comprising: (e) an application element for applying to the skin ultrasound at a frequency of from about 3 MHz to about 10 MHz and an intensity of from about 0.1 W/cm$^2$ to about 2 W/cm$^2$; and (f) a control element for controlling application conditions of the application element.

25 Claims, 10 Drawing Sheets

FOREIGN PATENT DOCUMENTS

| | | |
|---|---|---|
| JP | 11-269058 A | 10/1999 |
| JP | 11-335271 | 12/1999 |
| JP | 2001-106621 A | 4/2001 |
| JP | A-2002-012143 | 1/2002 |
| WO | WO 88/00001 A2 | 1/1988 |
| WO | WO 91/12772 A1 | 9/1991 |
| WO | WO 94/08655 A2 | 4/1994 |
| WO | WO 96/02276 A2 | 2/1996 |
| WO | WO 97/04832 A1 | 2/1997 |
| WO | WO 97/40679 A1 | 11/1997 |
| WO | WO 99/49841 A1 | 10/1999 |
| WO | WO 99/51295 A1 | 10/1999 |
| WO | WO 00/21605 A1 | 4/2000 |
| WO | WO 00/37029 A1 | 6/2000 |
| WO | WO 00/61083 A1 | 10/2000 |
| WO | WO 00/61098 A1 | 10/2000 |
| WO | WO 02/58665 A1 | 8/2002 |
| WO | WO 02/92046 A1 | 11/2002 |

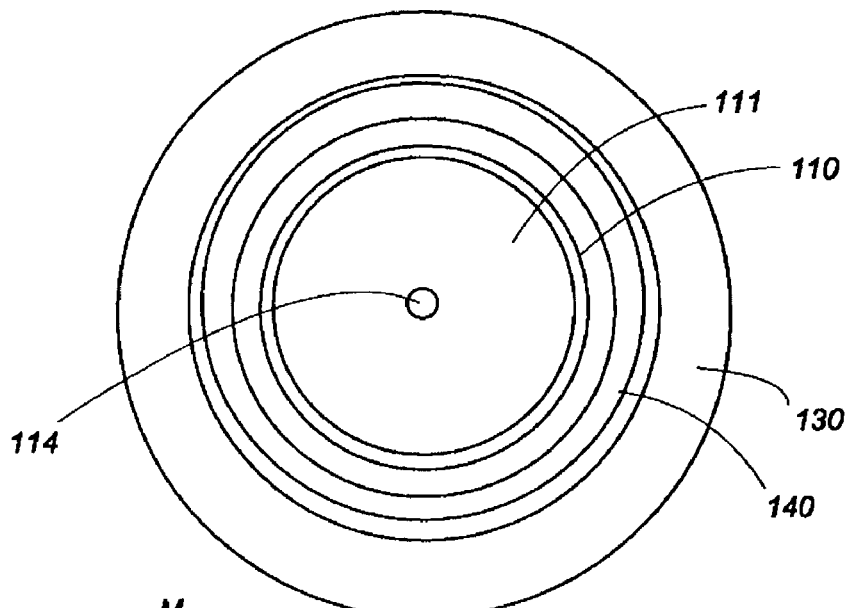
FIG. 8
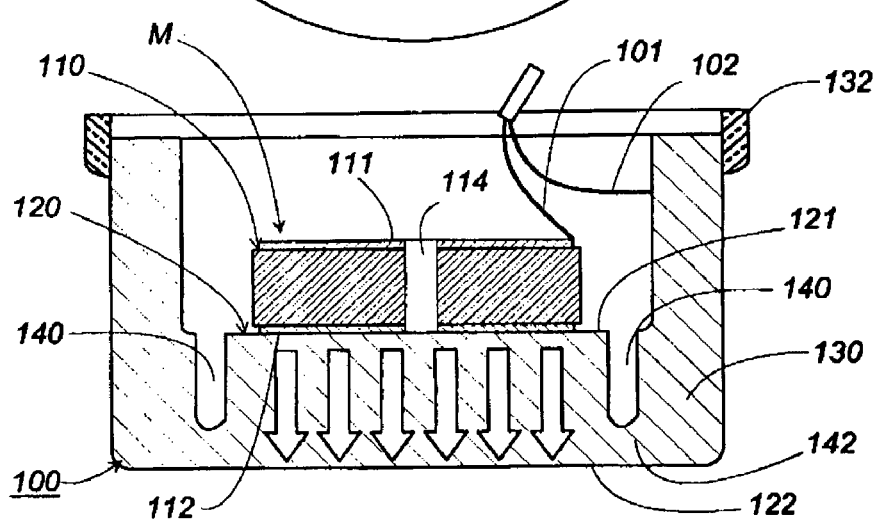
FIG. 9
FIG. 10 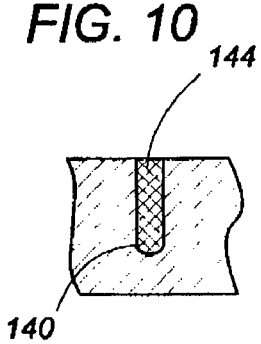 FIG. 11 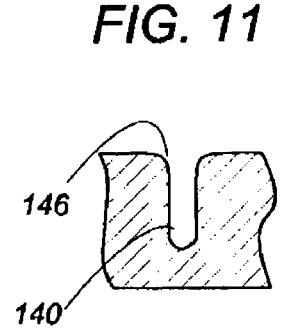 FIG. 12 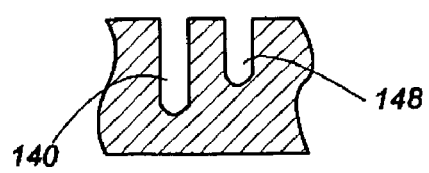

SKIN CARE DEVICE

CROSS REFERENCE TO RELATED APPLICATION

This application is a continuation in part of International Application No. JP03/00455 filed on Jan. 21, 2003.

FIELD OF THE INVENTION

The present invention relates to a skin care device that comprises a composition and an ultrasound applying apparatus. The device provides improved penetration of skin active agents to the skin, while also being safe for the general consumer to use. The present invention further relates to a method of treating the skin by applying the composition and an ultrasound of a certain frequency.

BACKGROUND

Various treatment for the skin are proposed for delaying, minimizing or even eliminating skin hyperpigmentation (age spots, freckles, blotches, darkening, uneven tone, and the like), wrinkling and other chronical changes typically associated with skin aging or environmental damage to human skin. Such treatment range from application of specialty cosmetics such as packs and masks, oral intake of vitamins, to chemical peeling, laser surgery, photofacial, and others. Generally, it is believed that effective treatment requires more time, physical, and financial commitment. There is a high desire for a treatment which is effective, but is safe and reasonably priced such that the consumer can provide the treatment by himself/herself. PCT application WO 98/51255 teaches an ultrasound application device which has multiple safety features suitable for use by a layperson without the aid of a specialist. Such type of treatment is attractive to the general consumer, as the treatment can be provided at home by the consumer at his/her discretion.

The use of ultrasound to deliver agents transcutaneously, generally termed "sonophoresis" or "phonophoresis", is known in the art, for example in GB publication 1577551, PCT publication WO 88/00001, PCT publication WO 91/12772, PCT publication WO 94/08655, U.S. Pat. No. 5,267,985, PCT publication WO 97/04832, U.S. Pat. No. 5,445,611, PCT publication WO 97/40679, PCT publication WO 99/51295, U.S. Pat. No. 6,066,123, Japanese patent publication A-11-335271, U.S. publication 2002-55702, and PCT publication WO 00/21605. The depth of penetration into skin of ultrasound is inversely related to the frequency. Ultrasound at lower frequency is believed to provide effect towards deeply into the tissue, thus is effectively used for diagnosis, while higher frequency is believed to provide more effect towards the surface of the skin. PCT publication WO 88/00001 teaches the use of ultrasound at a frequency of no more than about 2.5 MHz for effectively delivering drugs to the circulatory system. To provide an effect to the epidermis of the skin, for example improved penetration of active ingredients that benefit to the epidermis of the skin, ultrasound at higher frequency is effective. Copending Japanese patent application 2002-012143 describes use of higher frequencies for delivery of skin active agents.

For providing a skin care treatment that is safe and effective for the general consumer, further improvement is desired. For example, aqueous gel carriers that have been proposed for use with ultrasound application have been unsatisfactory in effective delivery of skin active agents to the basale epidermidis, and further unsatisfactory in providing good aesthetic/sensory benefits to the skin compared to cosmetic products. In another example, the ultrasound application devices have been unsatisfactory in providing safety features that effectively operate even when applying ultrasound at higher frequencies.

Based on the foregoing, there is a need for a skin care device or method which provides safe and effective skin care treatment benefit via the combined use of skin active agent and ultrasound application. Specifically, there is a need for a composition which, when used in combination with an ultrasound applying apparatus, can effectively deliver the ultrasound to the skin, is stable, while providing smoothness and moisturization to the skin without leaving the skin feel sticky. Meanwhile, there is a need for an ultrasound application apparatus which has a control element for providing the frequency and intensity of ultrasound at a safe and effective level.

None of the existing art provides all of the advantages and benefits of the present invention.

SUMMARY

The present invention is directed to a device for penetrating a skin active agent to the human body via the skin by the use of an ultrasound applying apparatus which applies ultrasound to the human body via the skin, comprising:
(1) a composition comprising:
  (a) a safe and effective amount of the skin active agent;
  (b) a viscosifying agent that provides the composition a viscosity of from about 1,000 mPas to about 1,000,000 mPas;
  (c) from about 0.1% to about 30% of a water-soluble humectant; and
  (d) an aqueous carrier;
  wherein the composition is substantially free of surfactants; and
(2) the ultrasound applying apparatus comprising:
  (e) an application element for applying to the skin ultrasound at a frequency of from about 3 MHz to about 10 MHz and an intensity of from about 0.1 W/cm$^2$ to about 2 W/cm$^2$; and
  (f) a control element for controlling application conditions of the application element.

The present invention is also directed to a method of treating the skin comprising the steps of: applying to the skin the aforementioned composition; and applying ultrasound to the surface of the skin by the aforementioned ultrasound applying apparatus; wherein the composition is used as a medium for applying ultrasound to the skin by the ultrasound applying apparatus.

These and other features, aspects, and advantages of the present invention will become evident to those skilled in the art from a reading of the present disclosure with the appended claims.

BRIEF DESCRIPTION OF THE FIGURES

While the specification concludes with claims particularly pointing out and distinctly claiming the invention, it is believed that the present invention will be better understood from the following description of preferred, nonlimiting embodiments and representations taken in conjunction with the accompanying drawings in which:

FIG. 8 is a top plan view of an applicator head of the above device;

FIG. 9 is a sectional view of the applicator head;

FIGS. 10 to 12 are partial views illustrating modified structure of the applicator head;

DETAILED DESCRIPTION

Figure 1:
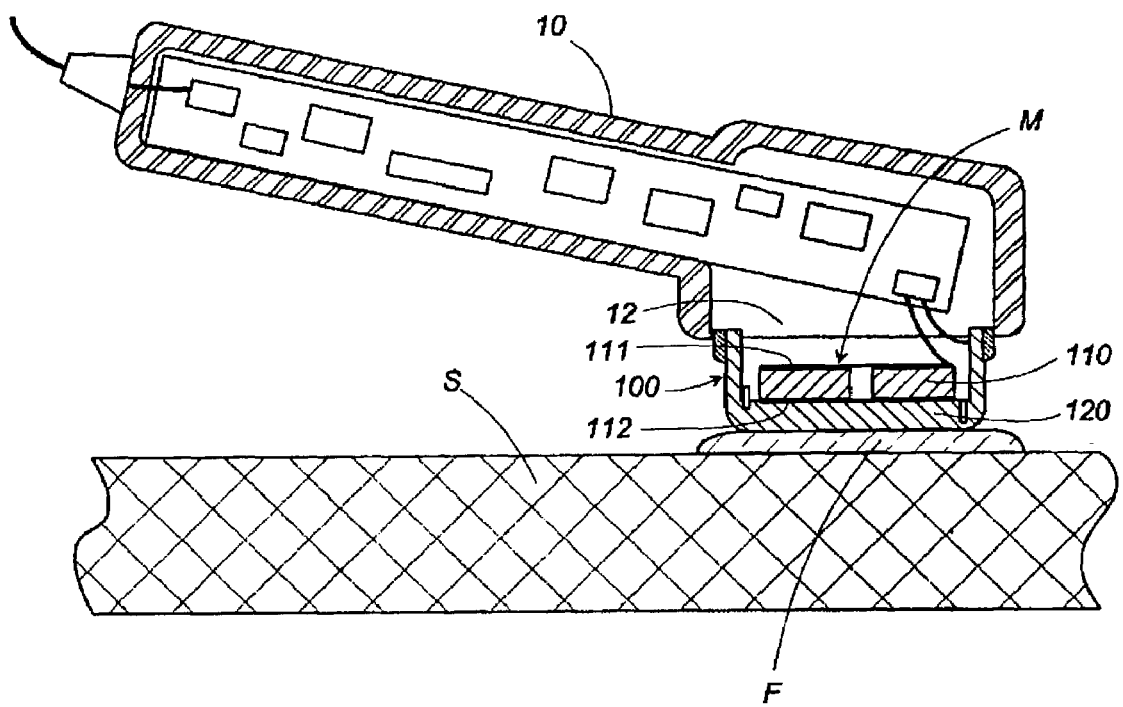
FIG. 1 is a front sectional view of an ultrasound applying skin care device in accordance with a preferred embodiment of the present invention.

While the specification concludes with claims particularly pointing out and distinctly claiming the invention, it is believed that the present invention will be better understood from the following description.

All cited references are incorporated herein by reference in their entireties. Citation of any reference is not an admission regarding any determination as to its availability as prior art to the claimed invention.

Herein, "comprising" means that other elements which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

Skin Care Device and Method of Use

The present device comprises a composition and an ultrasound applying apparatus, and provides skin care benefit in a safe and effective manner. The device provides improved penetration of skin active agents to the skin, while also being safe for the general consumer to use. The skin care benefit of the skin active agent contained in the composition is enhanced by the application of an ultrasound at a frequency of from about 3 MHz to about 10 MHz, thus the efficacy of treatment is greater than that compared to the independent use of the present composition.

In addition to the frequency, the intensity of the ultrasound is also important. Since the energy of higher frequency ultrasound is consumed at a shallower part of the skin, the heat generation in this area is greater. Thus, greater intensity generates greater heat, and skin disorders such as burns become a concern. On the other hand, a certain level of intensity is necessary for enhancing skin penetration of the skin benefit agent. In the present invention, the intensity of ultrasound is from about 0.1 W/cm$^2$ to about 2 W/cm$^2$ per surface area of the skin.

In the present device, the present composition is used as a medium for applying ultrasound to the skin by the present apparatus. Accordingly, when ultrasound is applied by the present apparatus, the present composition is existing in the space between the present apparatus and the skin, the amount of the present composition being sufficient for substantially filling such space, and for allowing the present apparatus to move along the surface of the skin. Preferably, the space between the present apparatus and the skin is devoid of air. Without being bound by theory, the penetration of the present composition is believed to be enhanced as a result of loosening of the intercellular lipid of the stratum corneum by the ultrasound application. Further, it is believed that the rheology of the present composition is particularly suitable for moving the present apparatus along the surface of the skin, while also effectively delivering the ultrasound, and maintaining a stable gel structure despite the vibration and heat emerged by the ultrasound application.

(1) The Composition (a) Skin Active Agent

The present composition comprises a safe and effective amount of a skin active agent. The term "skin active agent" as used herein, means an active ingredient which provides a cosmetic and/or therapeutic effect to the area of application on the skin, hair, or nails. The skin active agents useful herein include skin lightening agents, anti-acne agents, emollients, non-steroidal anti-inflammatory agents, topical anaesthetics, artificial tanning agents, antiseptics, anti-microbial and anti-fungal actives, skin soothing agents, sunscreening agents, skin barrier repair agents, anti-wrinkle agents, anti-skin atrophy actives, lipids, sebum inhibitors, sebum inhibitors, skin sensates, protease inhibitors, skin tightening agents, anti-itch agents, hair growth inhibitors, desquamation enzyme enhancers, anti-glycation agents, and mixtures thereof. In general, the present composition comprises from about 0.001% to about 30%, preferably from about 0.001% to about 10% of at least one skin active agent.

The type and amount of skin active agents are selected so that the inclusion of a specific agent does not affect the stability of the composition. For example, while water-soluble agents are preferable from a composition stability point of view, water-insoluble agents may also be included to the extent it can be dispersed with the viscosifying agent and or optional lower alkyl alcohol carrier, and thus does not affect the stability of the present composition. The term "water soluble" with regard to skin active agents herein, relate to compounds that are completely dissolved to make a transparent solution when dissolved in ample amount of water at ambient temperature.

Skin lightening agents useful herein refer to active ingredients that improve hyperpigmentation as compared to pre-treatment. Without being bound by theory, use of skin lightening agents for the present composition is particularly useful, as the frequency provided by the present apparatus effectively stimulate the epidermis, particularly the melanocyte region, wherein melanin is generated. The combined use of the skin lightening agent and ultrasonic wave application is believed to provide synergistic skin lightening benefit.

Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents are believed to be advantageous in that they may provide skin lightening benefit through different mechanisms. Preferably, the skin lightening agent comprises a water soluble skin lightening agent selected from ascorbic acid compounds, vitamin $B_3$ compounds, azelaic acid, gallic acid and its derivatives, hydroquinone, kojic acid, arbutin, mulberry extract, and mixtures thereof. In one preferred embodiment, a combination of ascorbic acid compounds and vitamin $B_3$ compounds are used.

Ascorbic acid compounds useful herein include, ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein includes, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include: magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

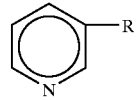

wherein R is —$CONH_2$ (e.g., niacinamide) or —$CH_2OH$ (e.g., nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and more preferred is niacinamide. In a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. Commercially available vitamin $B_3$ compounds that are highly useful herein include niacinamide USP available from Reilly.

Other skin active agents useful herein include those selected from the group consisting of panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof. Preferred are those which are water soluble.

(b) Viscosifying Agent

The present composition comprises a viscosifying agent that provides the composition a viscosity of from about 1,000 mPas to about 1,000,000 mPas, preferably from about 3,000 mPas to about 100,000 mPas. The polymers useful for providing the viscosifying agent herein are water soluble or water miscible polymers. The term "water soluble or water miscible" with regard to the viscosifying agents herein, relate to compounds that are dissolved to make a transparent solution when dissolved in ample amount of water with or without the aid of elevated temperature and/or mixing.

In one preferred embodiment, the viscosifying agent comprises a carboxylic acid/carboxylate copolymer and a cellulose derivative polymer. The combination of these polymers are believed to provide a composition that is transparent or translucent, while providing smoothness and moisturization to the skin without leaving the skin feel sticky. Other polymers compatible with the carboxylic acid/carboxylate copolymer and cellulose derivative polymer may also be included. In one highly preferred embodiment, the viscosifying agent is substantially made of only carboxylic acid/carboxylate copolymer and cellulose derivative polymer.

The present composition preferably comprises a carboxylic acid/carboxylate copolymer. The carboxylic acid/carboxylate copolymer keeps the composition relatively transparent and at a suitable viscosity without making the composition tacky or greasy upon use. Without being bound by theory, the carboxylic acid/carboxylate copolymer is also believed to provide a shear thinning property to the present composition. What is meant by shear thinning property is that a yield point exists within a typical shear stress applicable by the hand on the skin, and that the viscosity of the composition beyond the yield point significantly decreases to the extent such decrease is noticeable by the consumer.

Additionally, the carboxylic acid/carboxylate copolymer is capable of dispersing and stabilizing water insoluble components, such as water insoluble skin lightening agents in liquid form, in the present composition when such component is included.

The carboxylic acid/carboxylate copolymers herein are hydrophobically-modified cross-linked coplymers of carboxylic acid and alkyl carboxylate, and have an amphiphilic property. These carboxylic acid/carboxylate copolymers are obtained by copolymerizing 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

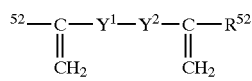

wherein $R^{52}$ is a hydrogen or an alkyl group having from about 1 to about 30 carbons; $Y^1$, indepedently, is oxygen, $CH_2O$, COO, OCO,

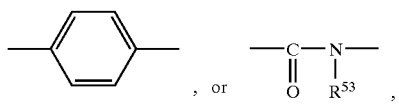

wherein $R^{53}$ is a hydrogen or an alkyl group having from about 1 to about 30 carbons; and $Y^2$ is selected from $(CH_2)_{m''}$, $(CH_2CH_2O)_{m''}$, or $(CH_2CH_2CH_2O)_{m''}$ wherein m" is an integer of from 1 to about 30. It is believed that, because of the alkyl group contained in the copolymer, the carboxylic acid/carboxylate copolymers do not make the composition undesirably sticky.

Suitable carboxylic acid/carboxylate copolymers herein are acrylic acid/alkyl acrylate copolymers having the following formula:

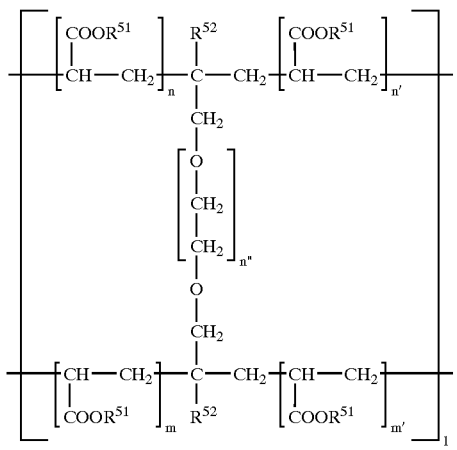

wherein $R^{51}$, independently, is a hydrogen or an alkyl of 1 to 30 carbons wherein at least one of $R^{51}$ is a hydrogen, $R^{52}$ is as defined above, n, n', m and m' are integers in which n+n'+m+m' is from about 40 to about 100, n" is an integer of from 1 to about 30, and l is defined so that the copolymer has a molecular weight of about 500,000 to about 3,000,000.

Commercially available carboxylic acid/carboxylate copolymers useful herein include: CTFA name Acrylates/C10–30 Alkyl Acrylate Crosspolymer having tradenames Pemulen TR-1, Pemulen TR-2, Carbopol 1342, Carbopol 1382, and Carbopol ETD 2020, all available from B. F. Goodrich Company.

Neutralizing agents may be included to neutralize the carboxylic acid/carboxylate copolymers herein. Nonlimiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof.

The present composition preferably comprises a cellulose derivative polymer. Without being bound by theory, it is believed the controlled amount of cellulose derivative polymer in the composition provides improved moisturization and smoothness to the skin without giving an undesirable tacky or sticky feeling.

Cellulose derivative polymers useful herein include methylcellulose, ethylcellulose, hydroxyethylcellulose, hydroxyethyl ethylcellulose, hydroxypropyl methyl cellulose, nitrocellulose, sodium cellulose sulfate, sodium carboxymethylcellulose, crystalline cellulose, cellulose powder, and mixtures thereof. Particularly preferred are hydroxyethylcellulose carboxymethylcellulose, and mixtures thereof. Commercially available compounds that are highly useful herein include hydroxyethylcellulose with tradename Natrosol Hydroxyethylcellulose, and carboxymethylcellulose with tradename Aqualon Cellulose Gum, both available from Aqualon.

The compositions of the present invention may further comprise an additional water soluble polymer for the viscosifying agent.

Additional water soluble polymers useful herein include anionic polymers and nonionic polymers. Useful herein are vinyl polymers such as cross linked acrylic acid polymers with the CTFA name Carbomer, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed (Cydonia oblonga Mill), starch (rice, corn, potato, wheat), algae colloids (algae extract), microbiological polymers such as dextran, succinoglucan, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyalkylene glycols having a molecular weight of more than about 1000 are useful herein. Useful are those having the following general formula:

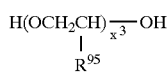

wherein $R^{95}$ is selected from the group consisting of H, methyl, and mixtures thereof. When $R^{95}$ is H, these materials are polymers of ethylene oxide, which are also known as polyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist. In the above structure, x3 has an average value of from about 1500 to about 25,000, preferably from about 2500 to about 20,000, and more preferably from about 3500 to about 15,000. Other useful polymers include the polypropylene glycols and mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9-M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available additional water soluble polymers highly useful herein include xanthan gum with tradename Keltrol series available from Kelco, Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, scieroglucan with tradename Clearogel SC11 available from Michel Mercier Products Inc. (NJ, USA), ethylene oxide and/or propylene oxide based polymers with tradenames CARBOWAX PEGs, POLYOX WASRs, and UCON FLUIDS, all supplied by Amerchol.

Additional water soluble polymers useful herein include amphoteric polymers. The amphoteric polymers useful herein are those including at least one cationic monomer and at least one anionic monomer; the cationic monomer being quaternary ammonium, preferably dialkyl diallyl ammonium chloride or carboxylamidoalkyl trialkyl ammonium chloride; and the anionic monomer being carboxylic acid. The amphoteric conditioning polymers herein may include nonionic monomers such as acrylamine, methacrylate, or ethacrylate.

Useful herein are polymers with the CTFA name Polyquaternium 22, Polyquaternium 39, and Polyquaternium 47. Such polymers are, for example, copolymers consisting of dimethyldiallyl ammonium chloride and acrylic acid, terpolymers consisting of dimethyldiallyl ammonium chloride and acrylamide, and terpolymers consisting of acrylic acid methacrylamidopropyl trimethylammonium chloride and methyl acrylate such as those of the following formula wherein the ratio of $n^6:n^7:n^8$ is 45:45:10:

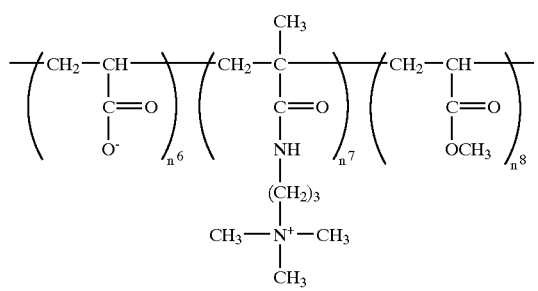

Highly preferred commercially available amphoteric polymers herein include Polyquaternium 22 with tradenames MERQUAT 280, MERQUAT 295, Polyquaternium 39 with tradenames MERQUAT PLUS 3330, MERQUAT PLUS 3331, and Polyquaternium 47 with tradenames MERQUAT 2001, MERQUAT 2001N, all available from Calgon Corporation.

Also useful herein are polymers resulting from the copolymerisation of a vinyl monomer carrying at least one carboxyl group, such as acrylic acid, methacrylic acid, maleic acid, itaconic acid, fumaric acid, crotonic acid, or alphachloroacrylic acid, and a basic monomer which is a substituted vinyl compound containing at least one basic nitrogen atom, such as dialkylaminoalkyl methacrylates and acrylates and dialkylaminoalkylmethacrylamides and acrylamides.

Also useful herein are polymers containing units derived from:

i) at least one monomer chosen from amongst acrylamides or methacrylamides substituted on the nitrogen by an alkyl radical, ii) at least one acid comonomer containing one or more reactive carboxyl groups, and iii) at least one basic comonomer, such as esters, with primary, secondary and tertiary amine substituents and quaternary ammonium substituents, of acrylic and methacrylic acids, and the product resulting from the quaternisation of dimethylaminoethyl methacrylate with dimethyl or diethyl sulfate.

The N-substituted acrylamides or methacrylamides which are most particularly preferred are the groups in which the alkyl radicals contain from 2 to 12 carbon atoms, especially N-ethylacrylamide, N-tert.-butylacrylamide, N-tert.-octylacrylamide, N-octylacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates.

(c) Water Soluble Humectant

The composition of the present invention comprises from about 0.1% to about 30%, preferably from about 0.1% to about 10% of a water soluble humectant. Water soluble humectants useful herein include polyhydric alcohols such as butylene glycol (1,3 butanediol), pentylene glycol (1,2-pentanediol) glycerin, sorbitol, propylene glycol, hexylene glycol, ethoxylated glucose, 1,2-hexane diol, 1,2-pentane diol, hexanetriol, dipropylene glycol, erythritol, trehalose, diglycerin, xylitol, maltitol, maltose, glucose, fructose; and other water-soluble compounds such as sodium chondroitin sulfate, sodium hyaluronate, sodium adenosin phosphate, sodium lactate, pyrrolidone carbonate, glucosamine, cyclodextrin, and mixtures thereof. Also useful herein include water soluble alkoxylated nonionic polymers such as polyethylene glycols and polypropylene glycols having a molecular weight of up to about 1000 such as those with CTFA names PEG-200, PEG-400, PEG-600, PEG-1000, and mixtures thereof.

In one preferred embodiment, the water-soluble humectant is substantially selected only from the group consisting of butylene glycol, pentylene glycol, and mixtures thereof. These humectants provide moisturizing effect to the skin without significantly deteriorating the penetration of the skin lightening agents of the present invention.

Commercially available humectants herein include: butylenes glycol with tradename 1,3-Butylene glycol available from Celanese, pentylene glycol with tradename HYDROLITE-5 available from Dragoco, glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate available from Chisso Corp, the same with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; polyethylene glycols with the tradename CARBOWAX series available from Union Carbide, and a mixture of glyceryl polymethacrylate, propylene glycol and PVM/MA copolymer with tradename Lubrajel Oil available from Guardian Lab.

(d) Aqueous Carrier

The compositions of the present invention comprise an aqueous carrier for providing a transparent or translucent composition, suitably called gels. The compositions of the present invention do not have a distinctive discontinuous phase, is not an emulsion, nor a liquid crystal. The present invention is substantially free of surfactants. When water-insoluble components are included in the present invention, such components are kept to an amount solubilizable/dispersible by, for example, carboxylic acid/carboxylate copolymers or lower alkyl alcohol.

The level and species of the carrier are selected according to the compatibility with other components, and other desired characteristic of the product. Carriers useful in the present invention include water and water solutions of lower alkyl alcohols. Lower alkyl alcohols useful herein are monohydric alcohols having 1 to 6 carbons, more preferably ethanol and isopropanol. Preferably, the present composition comprises at least about 70% water. Deionized water is preferably used. Water from natural sources including mineral cations can also be used, depending on the desired characteristic of the product.

The pH of the present composition is selected in view of the activity and stability of the skin lightening agents, and desired characteristic of the product. In one preferred embodiment where the skin lightening agent contains the combination of ascorbic acid compound and vitamin $B_3$ compound, the pH is preferably from about 5 to about 8. Buffers and other pH adjusting agents can be included to achieve the desirable pH.

Free of Surfactant

The present composition is substantially free of surfactants. Preferably, there is less than about 1% surfactant present, more preferably, there is less than about 0.5% present, still preferably, there is no surfactant purposely added to the composition. What is meant by surfactants herein are any compounds that drastically decrease the surface tension and form micelles or reverse micelles above the critical micelle concentration when added to the composition. Anionic, amphoteric, zwitterionic, nonionic, and cationic surfactants that provide cleaning and lather upon application to the skin are included herein.

Anionic surfactants herein include ethoxylated alkyl sulphates, alkyl ethoxy carboxylates, alkyl glyceryl ether sulphonates, acyl sarcosinates, alkyl ethoxysulphosuccinates, alpha sulphonated fatty acids, their salts and/or their esters, ethoxylated alkyl phosphate esters, ethoxylated alkyl glyceryl ether sulfonates, paraffin sulfonates and alkoxy amide sulfonates, alkyl sulphates, and mixtures thereof.

Amphoteric surfactants herein include, cocoamphocarboxypropionate, cocoamphocarboxy propionic acid, cocoamphoacetate, cocoamphodiacetate (otherwise referred to as cocoamphocarboxyglycinate), sodium lauroamphoacetate (otherwise referred to as sodium lauroamphocarboxyglycinate).

Zwitterionic surfactants herein include, alkyl betaines and amido betaines.

Nonionic surfactants herein include, not only those that provide cleaning and lather, but also nonionic surfactants that primarily provide emulsification benefits. Such nonionic surfactants include condensation products of alkylene oxides which fatty acids, such as alkylene oxide esters of fatty acids, the condensation products of alkylene oxides with 2 moles of fatty acids, such as alkylene oxide diesters of fatty acids, the condensation products of alkylene oxides with fatty alcohols, examples of which include PEG 40 hydrogenated castor oil, steareth 2, isoceteth-20, and oleth-20. Other nonionic surfactants herein are the condensation products of alkylene oxides with both fatty acids and fatty alcohol, wherein the polyalkyene oxide portion is esterified on one end with a fatty acid and etherified on the other end with a fatty alcohol. Other nonionic surfactants herein are alkyl glucosides and alkyl polyglycosides, polyhydroxy fatty acid amide surfactants, alkoxylated sugar esters and polyesters, and fatty acid amides.

Cationic surfactants herein include: ammonium halide compounds, including those having hydrophilic substituents.

Oily Component

In one preferred embodiment, the composition of the present invention contains oily components which are useful for providing moisturizing efficacy to the skin. The oily components herein are water-insoluble components, thus must be kept to an amount solubilizable/dispersible by, for example, carboxylic acid/carboxylate copolymers or lower alkyl alcohol. When included, the oily component is comprised at from about 0.1% to about 15%, preferably from about 0.5% to about 10%, of the entire composition.

A wide variety of suitable oil compounds are known and may be used herein and numerous examples can be found in Sagarin, Cosmetics, Science and Technology, 2nd Edition, Vol. 1, pp. 32–43 (1972). Nonlimiting examples of suitable oily components include $C_{1-30}$ alcohol esters of $C_{1-30}$ carboxylic acids and of $C_{2-30}$ dicarboxylic acids, hydrocarbon oils, Mono-, di- and tri- glycerides of $C_{1-30}$ carboxylic acids, silicone oils, mineral oil and petrolatums, vegetable oils and hydrogenated vegetable oils, animal fats and oils, silicone oils, aromatic oils, and mixtures thereof, preferably hydrocarbon oils, fatty acid esters, silicone oils, and mixtures thereof.

Hydrocarbon oils useful herein include these having from about 7 to about 40 carbons. Examples of these hydrocarbon materials include dodecane, isododecane, squalane, hydrogenated polyisobutylene, docosane (i.e., a $C_{22}$ hydrocarbon), hexadecane, and isohexadecane. Also useful are the $C_{7-40}$ isoparaffins, which are $C_{7-40}$ branched hydrocarbons. Preferred hydrocarbon oils are isohexadecane sold as Permethyl 101A available from Presperse, squalane, light paraffin, light isoparaffin, light liquid paraffin, light liquid isoparaffin (a commercially available hydrocarbon sold as Isoper G® by Exxon, Isoparaffin® 2028 by Idemitsu, Amoco Mineral Spirits® by Ashland).

Fatty acid esters useful herein include cetyl 2-ethylhexyl, isopropyl myristate, myristyl myristate, isopropyl palmitate, cholesterol; more preferably cetyl 2-ethylhexyl and myristyl myristate; and triglycerides such as caprylic/capric triglyceride, PEG-6 caprylic/capric triglyceride, and PEG-8 caprylic/capric triglyceride, Meadowfoam Seed Oil.

Silicone oils useful herein may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable silicone oils can be selected from a wide variety of silicones spanning a broad range of volatilities and viscosities. While nonvolatile polysiloxanes are preferred, a small amount of volatile polysiloxanes may also be used. Nonlimiting examples of suitable silicones are disclosed in U.S. Pat. No. 5,069,897, to Orr, issued Dec. 3, 1991, which is incorporated by reference herein in its entirety. Examples of suitable silicone oils include polyalkylsiloxanes, cyclic polyalkylsiloxanes, and polyalkylarylsiloxanes. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Suitable dimethicones include alkyl-substituted dimethicones such as cetyl dimethicone and lauryl dimethicone. Commercially available dimethiconols are typically sold as mixtures with dimethicone or cyclomethicone (e.g., Dow Corning® 1501 and 1503 fluids). Commercially available cyclic polyalkylsiloxanes include Dow Corning® 244 fluid, Dow Corning® 344 fluid, Dow Corning® 245, and Dow Corning® 345 fluid.

Additional Components

The compositions herein may further contain other additional components, which may be selected by the artisan according to the desired characteristics of the final product and which are suitable for rendering the compositions more cosmetically or aesthetically acceptable or to provide them with additional usage benefits.

The present composition may further include skin benefit agents in addition to the skin lightening agents. The term "skin benefit agent" as used herein, means an active ingredient which provides a cosmetic and/or therapeutic effect to the area of application on the skin, hair, or nails. The additional skin benefit agents useful herein include anti-acne agents, emollients, non-steroidal anti-inflammatory agents, topical anaesthetics, artificial tanning agents, antiseptics, anti-microbial and anti-fungal actives, skin soothing agents, sunscreening agents, skin barrier repair agents, anti-wrinkle agents, anti-skin atrophy actives, lipids, sebum inhibitors, sebum inhibitors, skin sensates, protease inhibitors, skin tightening agents, anti-itch agents, hair growth inhibitors, desquamation enzyme enhancers, anti-glycation agents, and mixtures thereof.

The present composition may further include preservatives and preservative enhancers such as water-soluble or solubilizable preservatives including Germall 115, methyl, ethyl, propyl and butyl esters of hydroxybenzoic acid, benzyl alcohol, sodium metabisulfite, imidazolidinyl urea, EDTA and its salts, Bronopol (2-bromo-2-nitropropane-1,3-diol) and phenoxypropanol; antifoaming agents; binders; biological additives; bulking agents; coloring agents; perfumes, essential oils, and solubilizers thereof; other natural extracts; compounds which stimulate collagen production; yeast fermented filtrates, and others.

(2) The Ultrasound Applying Apparatus

The ultrasound applying apparatus employed in the present invention includes a housing with an applicator head for applying the ultrasound to the user's skin, and a driver circuit that provides an electric pulse for actuating the applicator head to transmit the ultrasound to the skin. The applicator head is composed of a vibrator element generating the ultrasound, and a horn having a mounting face and a skin opposing face for use in contact with the skin. The horn carries the vibrator element on the mounting face to transmit the ultrasound to the skin. The vibrator element and the horn are integrated into a combined vibration mass that resonates with the electric pulse from the driver circuit, thereby transmitting resulting vibrations to the skin. The combined vibration mass gives a first electrically equivalent impedance when it is normally loaded by contact with the skin, and gives a second electrically equivalent impedance when it is unloaded. The apparatus includes a load detecting circuit which monitors whether the combined vibration mass give the first or second electrically equivalent impedance and provides a load detection signal only upon seeing the first electrically equivalent impedance. Also included in the apparatus is a control circuit which limits or stops the electric pulse when the load detection signal is not received within a predetermined time period. The combined vibration mass has a structure that restrains vibrations at a center portion of the vibration mass in order to reduce a parasitic resonance, thereby differentiating the first electrically equivalent impedance from the second electrically equivalent impedance. Thus, the load detecting circuit can successfully judge whether the applicator head is in contact with or out of contact from the skin, whereby the control circuit can be made reliable to limit the ultrasonic vibrations from being generated when the applicator head is unloaded. The control circuit is designed to receive the first electrically equivalent impedance and constitute the control element that varies the intensity of the ultrasound generated at the vibrator element in accordance with the magnitude of the first electrically equivalent impedance. As the first electrically equivalent impedance will vary depending upon a pressure at which the horn or the combined vibration mass is held against the user's skin, the device can vary the effect or the strength of the ultrasound being applied to the skin depending upon the pressure, thereby applying the ultrasound optimally to the user's skin for enhanced skin care result.

Preferably, the vibrator element is composed of a piezoelectric element in the form of a circular disc having flat upper and lower end faces provided respectively with upper and lower electrodes across which the electric pulse is applied. At least one of the upper electrode, the lower electrode, and the piezoelectric element has a center opening which is responsible for restraining the vibrations at the center of the combined vibration mass.

In addition to the center opening, at least one of the upper and lower electrodes may be dimensioned to have a diameter smaller than that of the piezoelectric element to leave the peripheral portion of the piezoelectric element uncovered also for reducing undesired vibrations around the periphery of the piezoelectric element.

Alternatively, at least one of the upper and lower electrodes is divided by at least one slit into a plurality of identical segments. The slit extends diametrically to leave the center and the diametrically extending band portion of the piezoelectric element uncovered for restraining the vibrations at the center of the vibration mass.

Instead of providing the diametrically extending slit, at least one of the upper and lower electrodes may be configured to have at least one slit that uncovers the center portion of the piezoelectric element for the same purpose of restraining the vibrations at the center of the vibration mass.

In combination with or separately from the provision of the center opening in at least one of the upper electrode, the lower electrode, and the piezoelectric element, the horn may be configured to have a center hole in the form of a through-hole or cavity for restraining the vibrations at the center of the vibration mass.

Further, instead of being formed with the center opening, the upper electrode may be covered with an elastic member that absorbs the vibrations at the center portion of the vibration mass for reducing the parasitic resonance.

Still further, the upper electrode may be covered on its center with a solder bulk for electrical connection of the upper electrode to a lead wire leading from the driver circuit. The solder bulk adds a weight to the center of the combined vibration mass for restraining the vibrations at the center portion thereof.

Further, the horn is preferred to be formed as an integral part thereof with a rim which surrounds the horn and which is adapted to secure the horn to the housing. Defined between the horn and the rim is a restrictor which restricts the ultrasound from propagating towards the rim, thereby concentrating the ultrasound to the horn for effectively transmitting the wave to the skin through the horn. The restrictor may be in the form of a cavity formed along the boundary between the horn and the rim.

Still further, the apparatus is preferred to include a motion detecting circuit which monitors whether the combined vibration mass is moving and provides a motion detection signal when the vibration mass is so moving. The control circuit is connected to receive the motion detection signal and controls the driver circuit to stop or limit the electric pulse when the motion detection signal is not continuous over a critical time duration even in the presence of the load detection signal being detected within the predetermined time period.

Now, the ultrasound applying apparatus utilized in the above device will be discussed in detail with reference to the attached drawings.

As shown in FIG. 1, the ultrasound applying apparatus a hand-held grip housing 10 provided at its one end thereof with an applicator head 100 which is adapted in use to contact with a user's skin for applying ultrasound thereto. The applicator head 100 is composed of a vibrator element 110 in the form of a piezoelectric element generating the ultrasound, and a horn 120 transmitting the ultrasound to the skin S. The piezoelectric element is shaped into a circular disc having a flat upper surface and a flat lower surface which are covered respectively with upper and lower electrodes 111 and 112 across which an electric pulse is applied for generating the ultrasound vibration. The vibrator element 110 and the horn 120 are integrated into a combined vibration mass M which is caused by the electric pulse to resonate for generating and applying the resonant ultrasound vibration to the skin S. Preferably, the apparatus is designed to generate the ultrasound having a frequency of 3 MHz to 10 MHz and transmitted to the skin at an intensity of 0.1 W/cm$^2$ to 2.0 W/cm$^2$. Prior to applying the ultrasound, the composition F is spread over the skin to occupy the space between the horn 120 and the skin S, as shown in FIG. 1.

Figure 2A:
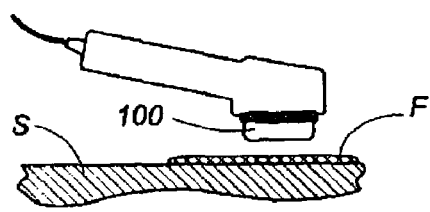
FIGS. 2A to 2C show improper use conditions of above device.
Figure 2B:
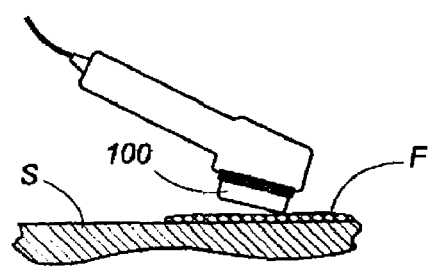
Figure 2C:
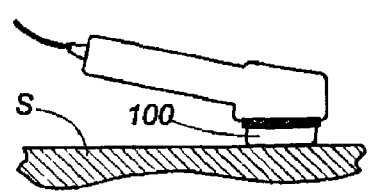

As will be explained later in details, the apparatus is equipped with a safe-guard for limiting or stopping the ultrasonic vibrations being transmitted to the skin when the applicator head 100 is not in a normally loaded condition of FIG. 1, i.e., the applicator head is held in any one of improper conditions. As shown in FIGS. 2A to 2C, the improper conditions include an unloaded condition where the applicator head 100 is away from the skin (FIG. 2A), a partial contact condition where the applicator head 100 is placed only partially against the skin (FIG. 2B), and a direct contact condition where the applicator head 100 is placed against the skin without using the composition F at the interface therebetween (FIG. 2C).

Figure 3:
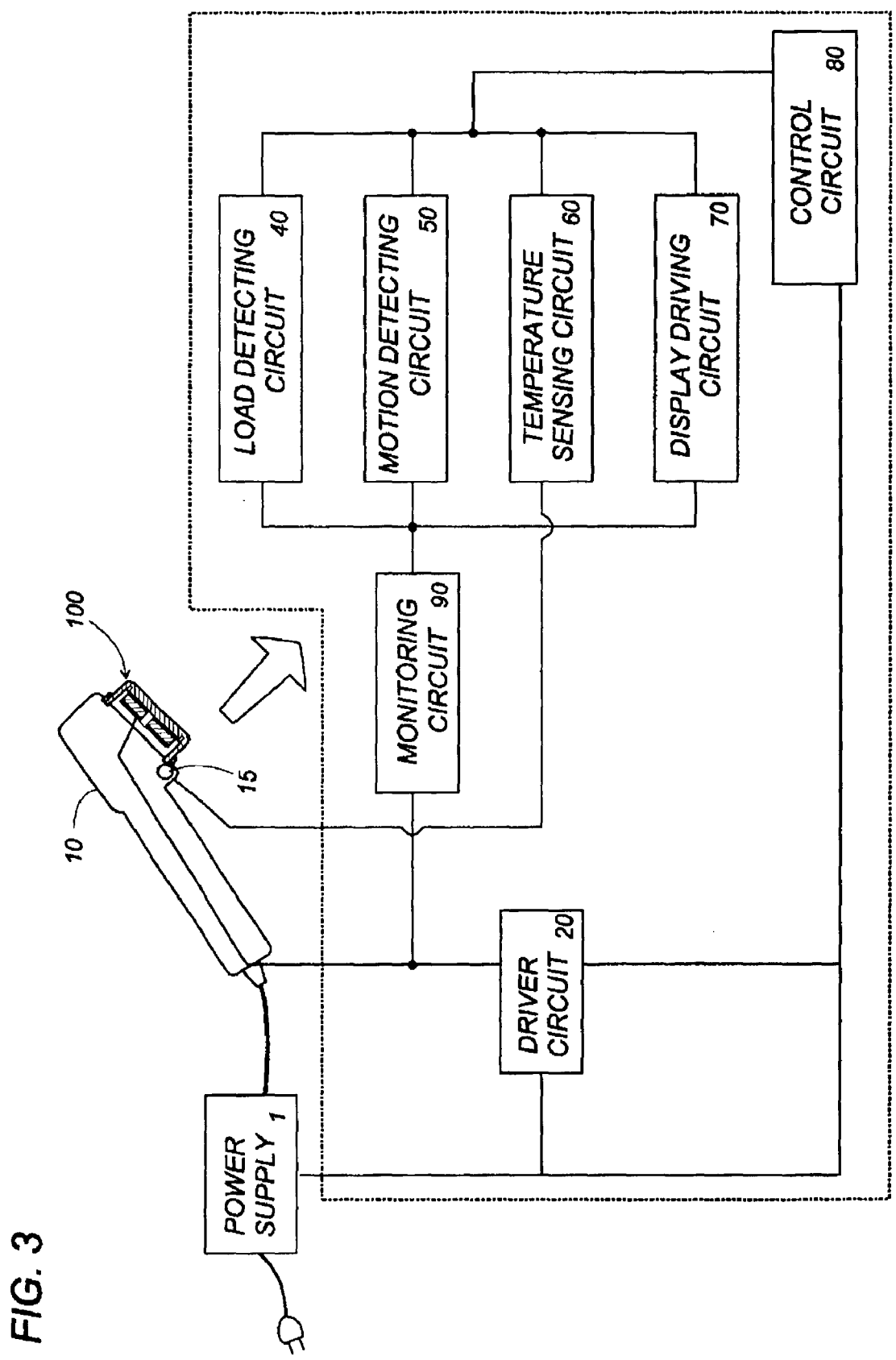
FIG. 3 is a block diagram of an electric circuitry of the above device.

As shown in FIG. 3, the apparatus includes a driver circuit 20 for providing the electric pulse across the electrodes 111 and 112 of the piezoelectric element 110, a load detecting circuit 40 for detection a load condition of the applicator head 100, a motion detecting circuit 50 for detection of a motion of the applicator head 100, a temperature sensing circuit 60 for sensing a temperature of the piezoelectric element 110, a display driver circuit 170 for displaying operating conditions of the apparatus, and a control circuit 80 for control of the above circuits. The driver circuit 20 is energized by a power supply 1 accommodated within a separate power pack 2 for converting a commercial AC line voltage into a DC voltage. Also included in the apparatus is a monitoring circuit 90 for monitoring the ultrasound being generated and applied to the user's skin based upon an electrically equivalent impedance of the combined vibration mass M.

The apparatus 10 is designed to generate the ultrasound while the horn 120 is kept substantially in contact with the use's skin. For this purpose, the load detecting circuit 40 is provided to detect whether a suitable load is applied as a consequence of the horn 120 being in contact with the user's skin via the composition F. When the horn 120 is not in contact with the skin and fails to transmit the ultrasound successfully, the load detecting circuit 40 determines that the horn 120 or the vibration mass M is not loaded and restricts the generation of the ultrasound. The details of the load detection realized in the present invention will be discussed later. In use, it is desirable to move the applicator head 100, i.e., the combination mass slowly across the skin when applying the ultrasound. Otherwise, when the applicator head 100 stays at a portion over a long period, there is a potential hazard of causing a cold burn in the skin. In view of this, the motion detecting circuit 50 is provided to enable the continuous ultrasound application when the applicator head 100 is moving at a suitable rate and otherwise disable or limit the ultrasound generation. In addition, the control circuit 80 includes a timer which stops generating the ultrasound after the apparatus is utilized over a preset time. That is, the timer will count a time only when the load detection signal from the load detecting circuit 40 indicates that the applicator head 100 is kept in the normal contact with the skin and when the motion detection signal from the motion detecting circuit 90 indicates that the applicator head 100 does not stay at a portion over a long time. The timer operates to continue generating the ultrasound over the preset time. Also, after the preset time is elapsed, the control circuit 80 gives an instruction to stop providing the electric power to the driver circuit 20, ceasing the ultrasound generation.

When the vibration mass suffers from abnormal vibrations with an attendant temperature rise due to malfunction of the driver circuit 20 or the like, the temperature sensing circuit 60 is responsive to an output from a temperature sensor 15 located adjacent the horn 120 for providing an output indicative of abnormal temperature rise to the control circuit 80 which in turn responds to stop the driver circuit 20.

Figure 4:
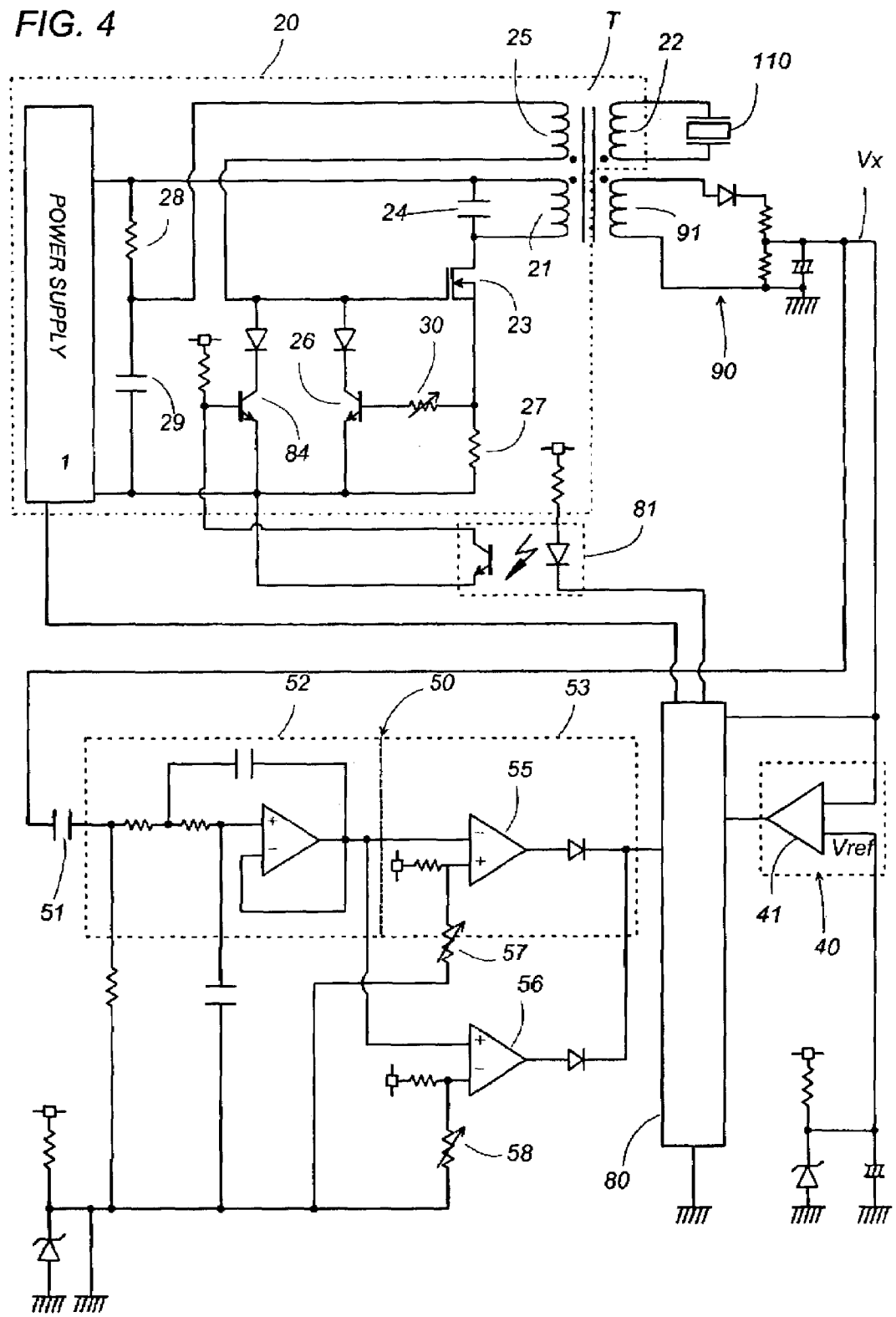
FIG. 4 is a circuit diagram illustrating a driver circuit, a load detecting circuit, a motion detecting circuit of the above circuitry.

As shown in FIG. 4, the driver circuit 20 includes an inverter which converts DC voltage from the power supply 1 into an AC voltage. Provided at the output end of the inverter is a transformer T with a primary winding 21 and a secondary winding 22. The primary winding 21 is connected in series with FET 23 and a current sensing resistor 27 across the power supply 1, and is cooperative with a capacitor 24 to form a parallel resonant circuit which provides a resonant voltage across the primary winding 21 upon turning off of FET 23. The piezoelectric element 110 is connected across the secondary winding 22 so as to effect the ultrasound vibrations by the AC voltage or the electric pulse induced at the secondary winding 22. A feedback winding 25 is coupled to the primary winding 21 to feedback the output of the driver circuit to FET 23. A bipolar transistor 26 is connected in a gate-emitter path of FET 23 for control of FET 23. Connected across the power supply 1 is a series combination of a starting resistor 28 and a capacitor 29 of which connection is connected through the feedback winding 25 to a gate of FET 23 to give a bias thereto. When capacitor 29 is charged by the power supply 1 to develop a voltage reaching a threshold of FET 23, FET becomes conductive to lower the drain voltage of FET 23. At this time, the feedback winding 25 generates a feedback voltage applied to the gate of FET 23, thereby increasing the current flowing through the FET. Subsequently when a voltage developed across current sensing resistor 27 reaches a predetermined level in correspondence to the increasing current through FET, transistor 26 becomes conductive to turn off FET 23. Whereby, the resonant circuit of primary winding 21 and capacitor 24 becomes active to make a resonance. At the end of one cycle of the resonance, the feedback voltage induced at feedback winding 25 reaches a voltage of turning on the gate of FET 23, thereby again making the FET conducive. The above operations are repeated to maintain the resonant voltage or the electric pulse so as to oscillate the piezoelectric element 110. The frequency of the resonant circuit is set variable in the range of 3 MHz to 10 MHz.

Figure 5:
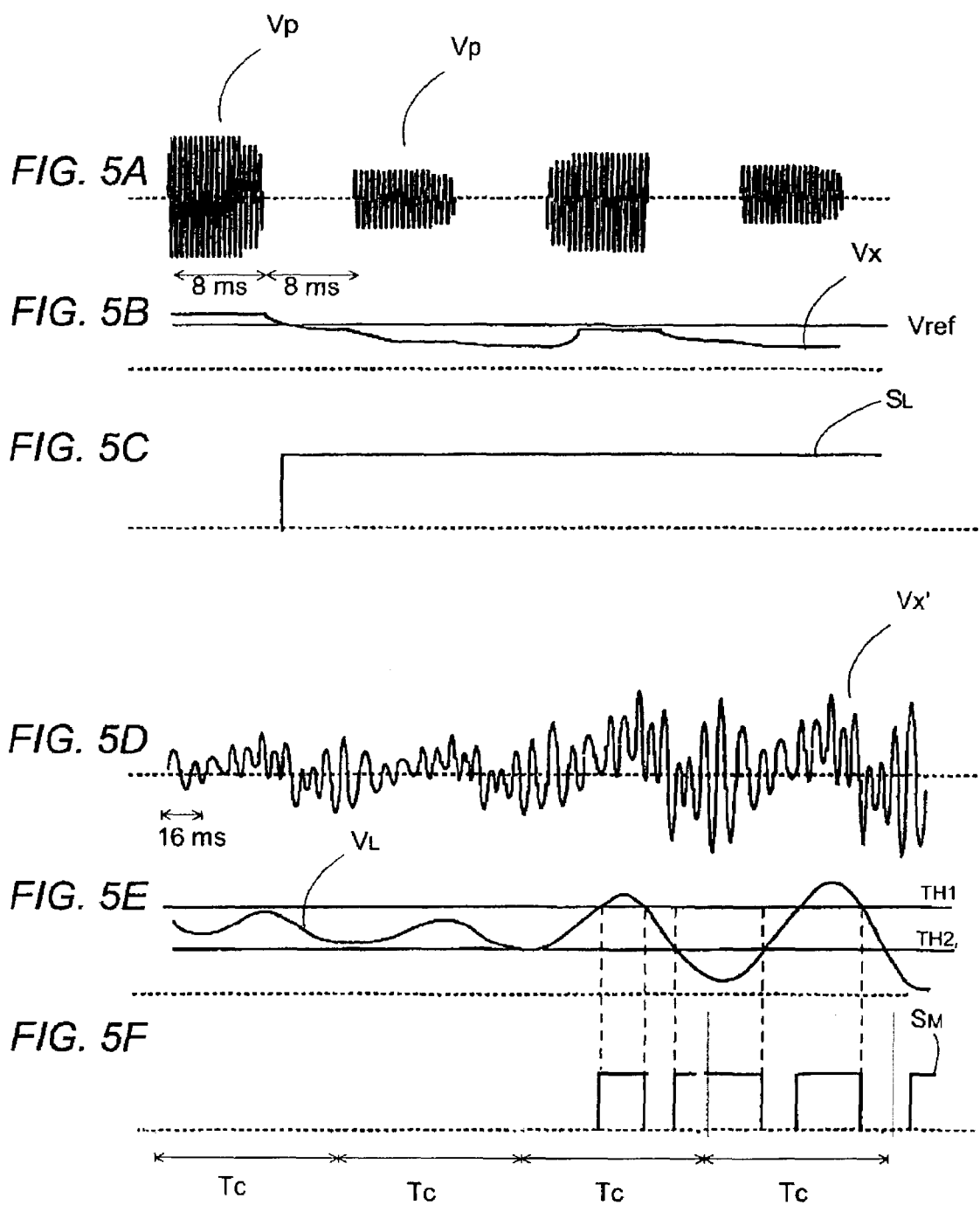
FIGS. 5A to 5F are waveform charts illustrating the operation of the load detecting circuit and the motion detecting circuit.

Connected between the base of transistor 26 and resistor 27 is a variable resistor 30 of which value is varied in order to adjust a timing of turning on transistor 26 for regulating the resonant frequency. It is noted in this connection that the resonant circuit is controlled by the control circuit 80 to give an intermittent oscillation having a rest period between adjacent pulse series Vp, as shown in FIGS. 5A and 5B.

The transformer T includes an auxiliary winding 91 which is cooperative with a rectifier circuit that rectifies the output of auxiliary winding 91 to constitute the monitoring circuit 90 which gives a monitoring output indicative of a condition of the ultrasound being applied to the user's skin. The monitoring output Vx includes low frequency components which are given as a result of moving the applicator head 100 and of which frequency is lower than that of the ultrasonic vibration. More precisely, the voltage appearing across auxiliary winding 91 includes low frequency components originating from a variation in electrically equivalent impedance of the combined vibration mass M upon contact with the load and originating from rubbing sounds appearing in response to the applicator head 100 moving across the skin of the user's skin, in addition to high frequency components indicative of the ultrasound vibrations. The monitoring output Vx is obtained by rectification of voltage appearing across auxiliary winding 91, and is fed to the load detecting circuit 40 and the motion detecting circuit 50 for making the load detection and the motion detection.

The load detecting circuit 40 has a comparator 41 which compares the monitoring output Vx from the monitoring circuit 90 with a reference level Vref. The monitoring output Vx has a waveform pattern as shown in FIG. 5B. When monitoring output Vx becomes lower than the reference level Vref, the comparator 41 provides a H-level load detection signal SL to the control circuit 80 as indicative of that the applicator head 100 is kept in the normal contact with the user's skin. When the load detection signal SL is not acknowledged continuously over a predetermined time period, the control circuit 80 stops operating the driver circuit 20 or disables the power supply 1. In this embodiment, the load detection signal SL is generated when the monitoring output Vx is lower than the reference level Vref in consideration of that the resonant voltage is lowered by the presence of the load, i.e. the increased impedance of the combined vibration mass M.

In addition, the output Vx indicative of the impedance of the combined vibration mass M is fed also to the control circuit 80. When the output Vx is equal to the reference level Vref or greater, the control circuit 80 operates to vary the output voltage of the power supply 1 a reverse proportion to the magnitude of the output Vx. That is, the combined vibration mass M is held against the user's skin at a greater pressure, the control circuit 80 acts to lower the intensity of the ultrasound being applied to the skin, and vice versa. With this result, the ultrasound can be adjusted depending upon the pressure at which the combined vibration mass M is held against the skin, thereby transmitting the ultrasound at an optimal intensity for enhanced skin care effect.

It is possible that resonant circuit of different configuration may vary the impedance characteristic of the combined vibration mass M in order to break the impedance matching with the resonant circuit, thereby causing the monitoring output to increase in the presence of the load. In this case, it is made to provide the load detection signal SL when the monitoring output Vx exceeds the reference level Vref. Also, it is equally possible to limit or reduce the ultrasound energy upon detection of the no-load condition.

Further, the monitoring output Vx is fed through a capacitor 51 to the motion detecting circuit 50 in the form of an output Vx', as shown in FIG. 5D. The motion detecting circuit 50 includes a low-pass filter 52 and a judging circuit 53. The output Vx' is removed of high frequency components through the filter 52 to give a low frequency output VL free from the components not caused by the motion of the applicator head 100, as shown in FIG. 5E. Thus obtained low frequency output VL is fed to two comparators 55 and 56 of the judging circuit 53 and compared respectively with individual thresholds TH1 and TH2 (TH1>TH2) to provide to the control circuit 80 a H-level motion detection signal SM (shown in FIG. 5F) over a period in which the output VL is higher than the threshold TH1 or lower than the threshold TH2. TH1 and TH2 can be adjusted by variable resistors 57 and 58. The control circuit 80 counts the time period of the H-level motion detection signal SM within a predetermined duration Te (for example, 15 seconds) and determines that the applicator head 100 has moved suitably when the sum of the counted times within the duration Tc exceeds a predetermined reference. Otherwise, the control circuit 80 determines that no suitable motion has been made and provides a limit signal of limiting the driver circuit 20. The driver circuit 20 includes a transistor 84 which is connected in parallel with transistor 26 across gate-source path of FET 23 and which is connected to the control circuit 80 through a photo-coupler 81. Thus, upon receiving the limit signal from the control circuit 80, the transistor 84 is turned on to thereby turn off FET 23 for disabling the driver circuit 20. Although the limit signal acts to stop the driver circuit 20 in this embodiment, the present invention is not limited to this feature and may be arranged to control the driver circuit 20 or power supply 1 to reduce the ultrasonic vibration energy.

Figure 6:
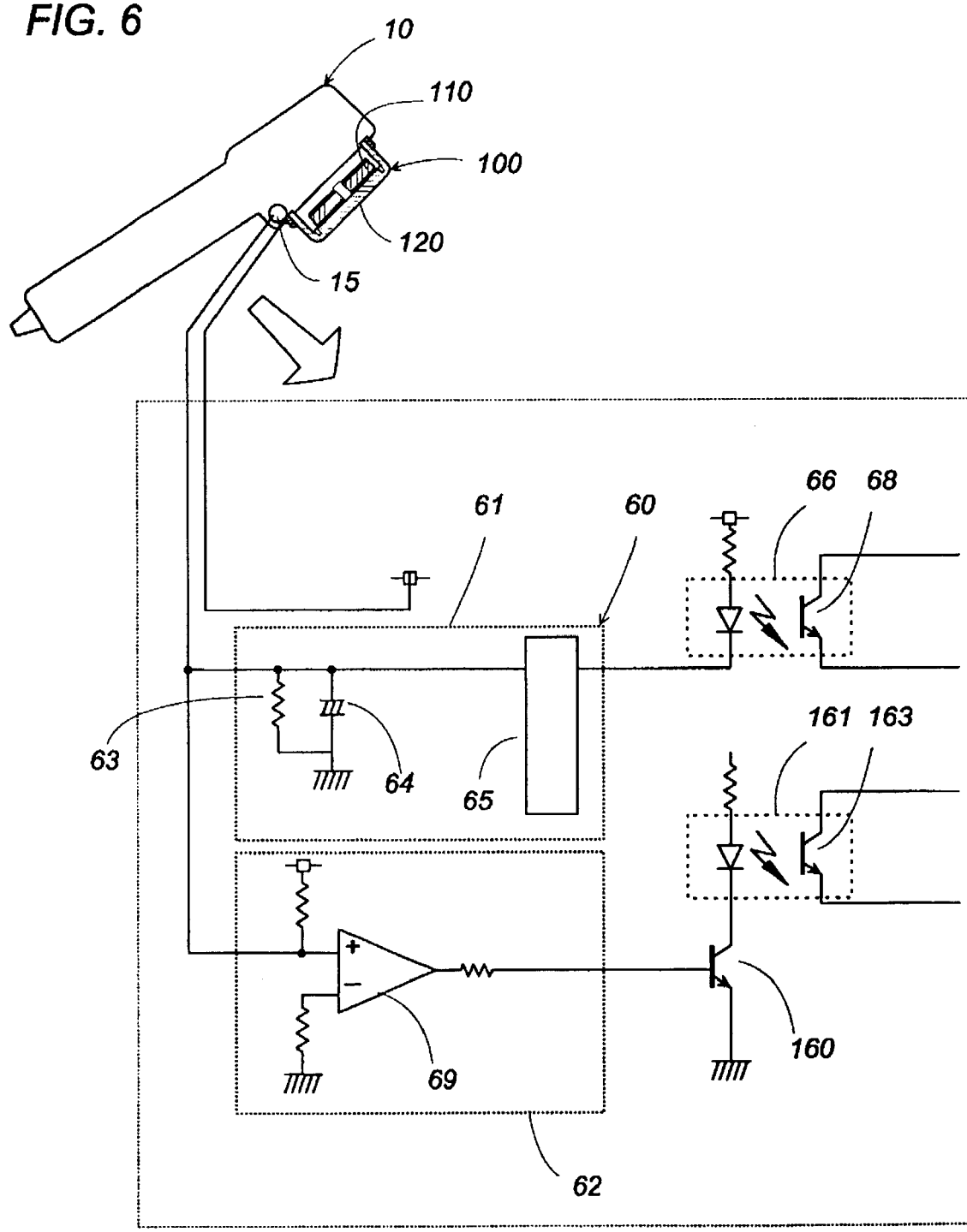
FIG. 6 is a circuit diagram illustrating a temperature sensing circuit of the above circuitry.

As shown in FIG. 6, the temperature sensing circuit 60 includes a first temperature sensing unit 61 and a second temperature sensing unit 62 both receiving an output from a thermistor 15 for temperature sensing. First temperature sensing unit 61 has a temperature controller 65 to which the output from thermistor 15 is fed through a resistor 63 and a capacitor 64. When the temperature sensed at thermistor 15 is found to exceed a predetermined reference temperature, the temperature controller 65 issues a stop signal to the driver circuit 20 through a photo-coupler 66. The photo-coupler 66 has a transistor 68 which is connected in a base-emitter path of the transistor 84, so that the stop signal causes the transistor 84 to turn on for stopping the oscillation of the driver circuit 20. A hysterics is given to the temperature control such that, after the temperature of the horn 120 sensed by thermistor 15 goes high above the reference temperature, the driver circuit 20 is enabled to resume the oscillation only after the sensed temperature goes below a temperature level which is lower than the reference temperature. When the sensed temperature goes below the temperature level, the temperature controller 65 responds not to issue the stop signal, thereby resuming the oscillation at the driver circuit 20. The second temperature sensing unit 62 includes a comparator 69 which operates to turn on a transistor 160 when the temperature sensed at thermistor 15 exceeds a predetermined reference, thereby turning on a transistor 163 of a photo-coupler 161 and consequently disabling the power supply 1 connected to transistor 163. The predetermined reference for the comparator 69 is set to be higher than the reference temperature of the temperature controller 65 for stopping the ultrasonic oscillation as a safeguard in response to the horn 120 being abnormally heated even if the temperature controller 65 made of a microprocessor should fail to operate.

Figure 7:
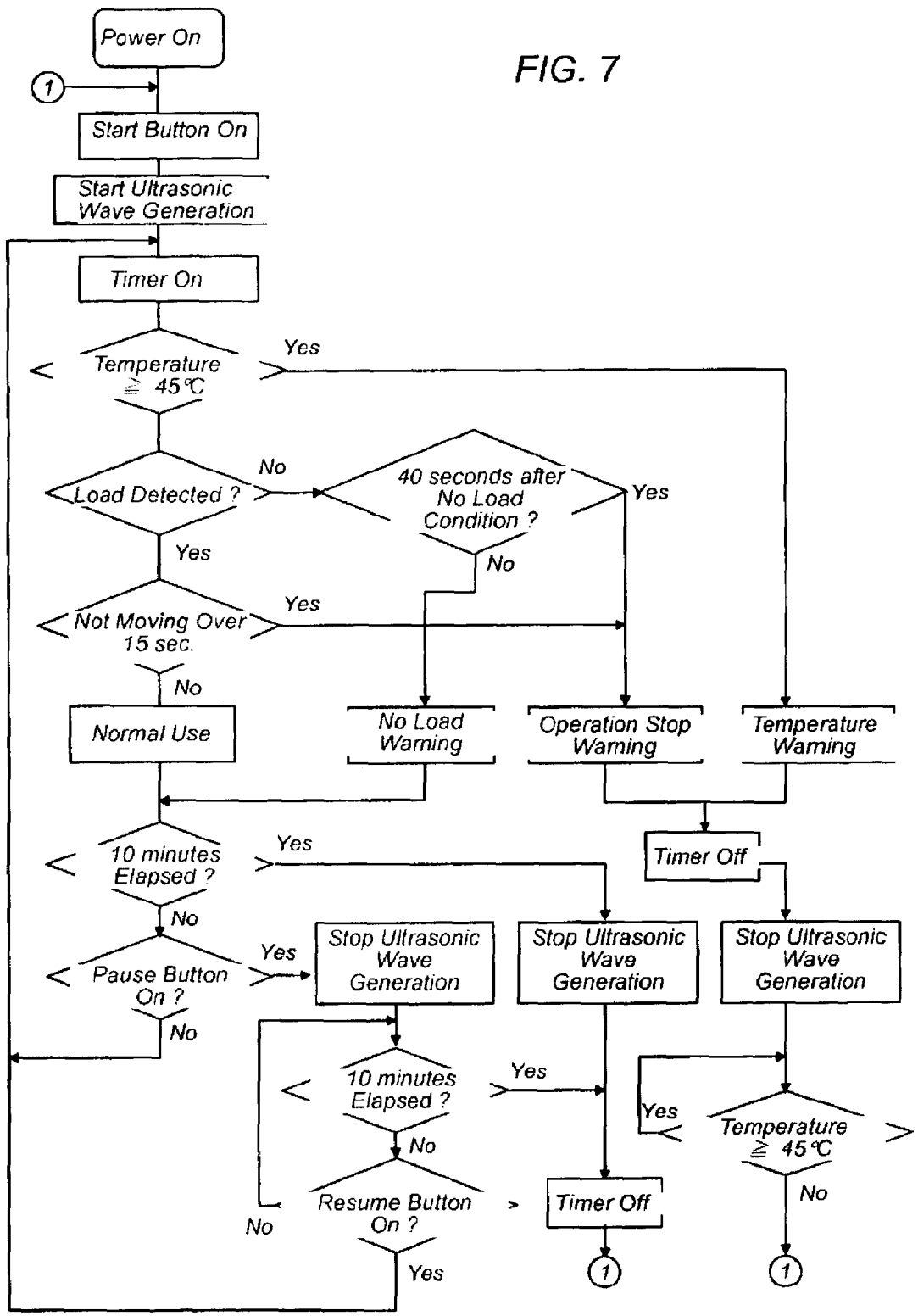
FIG. 7 is a flow chart illustrating the operations of the device.

Operation of the ultrasonic apparatus is now explained with reference to FIG. 7. After turning on a power switch, pressing of a start button actuates the driver circuit 20, causing the piezoelectric element 110 to start generating the ultrasound, and starting the timer. At this time, the temperature sensing is made for the horn 120 so that when the first temperature sensing unit 61 sees the temperature exceeding, for example, 450, the display driving circuit 70 gives the temperature warning that the horn 120 is over-heated, and causing the timer as well as the driver circuit 20 to stop. When the sensed temperature is found to be less than 45° C. at a step after starting the timer, the load detection is available, and subsequently the motion detection is available provided that the load detection signal is issued as indicative of that the applicator head 100 is loaded. When no load detection signal is issued, a no-load warning is displayed for a limited time period of 40 seconds, for example, prompting the user to make the applicator head 100 in contact with the skin. After elapse of 40 seconds with no load detection signal, a control is made to display a warning of stopping the operation and stop the timer and the ultrasound generation. The motion detection is made in the presence of the load detection signal so that, when the motion detection signal is issued within, for example, 15 seconds, a display of normal operation is made and a count-down instruction is given to the timer. After the elapse of a predetermined operation time, say, 10 minutes in this condition, the driver circuit is stopped. When a pause button is pressed within 10 minutes, the driver circuit is stopped but with the timer operating continuously to count down. When a restart button is pressed within the 10 minutes, the driver circuit resumes generating the ultrasound.

Although the above embodiment is so designed that the control circuit disables the driver circuit when no load or no motion is detected, the present invention is not limited to this feature and is designed to reduce the ultrasound energy upon such detection.

Now referring to FIGS. 8 and 9, the details of the applicator head 100, i.e., the combination of the piezoelectric element 110 and the horn 120 will be discussed. The piezoelectric element 110 is made of a ceramic and shaped into the circular disk having a uniform thickness and being provided on its upper and lower faces respectively with the upper and lower electrodes 111 and 112. The horn 120 is made of aluminum and is shaped into a circular disk having a surface area slightly larger than the piezoelectric element 110 and having a uniform thickness. The electric pulse from the driver circuit 20 is applied across the electrodes 111 and 112 by way of lead wires 101 and 102 respectively soldered to the upper electrode 111 and the horn 120, as shown in FIG. 9. The horn 120 is formed as an integrally part thereof with a tubular rim 130 which surrounds the horn 120. The rim 130 projects upwardly from the periphery of the horn 120 and is secured at its upper end to the housing 10 to support the applicator head 100 to the housing. The upper end of the rim 130 fits snugly into a mouth 12 of the housing 10 with an elastic damper ring 132 interposed therebetween. The horn 120 has a flat mounting face 121 for carrying thereon the piezoelectric element 110 in an intimate contact relation, and a flat skin opposing face 122 for contact with the skin through the composition F spread on the skin S. The piezoelectric element 110 is secured to the horn 120 such that they are integrated into the combined vibration mass M which resonates with the electric pulse from the driver circuit 20 to generate the ultrasound to be transmitted to the skin. A restrictor 140 in the form of a cavity extends between the horn 120 and the rim 130 in order to restrict the ultrasound vibrations from propagating towards the rim 130, thereby concentrating the ultrasound effectively to the user's skin, as indicated by arrows in FIG. 9. That is, the cavity 140 acts to isolate the rim 130 substantially from the combined vibration mass M of the piezoelectric element 110 and the horn 120 with regard to the ultrasound vibrations. As a result of forming the cavity 140, a bridge 142 of reduced thickness remains for connection of the horn 120 and the rim 130. The reduced thickness (t) of the bridge 142 is selected to be other than an integral multiple of one-fourth of the wavelength of the ultrasound ($t \neq n \cdot \lambda/4$, where n is an integer)) for effectively restricting the ultrasound vibrations from propagating towards the rim 130. As shown in FIGS. 10 and 11, the cavity 140 may be filled with a suitable medium 144 for blocking the ultrasound vibrations, or may be finished with rounded edges 146. Further, as shown in FIG. 12, an additional cavity 148 of different depth may be formed in a concentric relation to the cavity 140.

Figure 13:
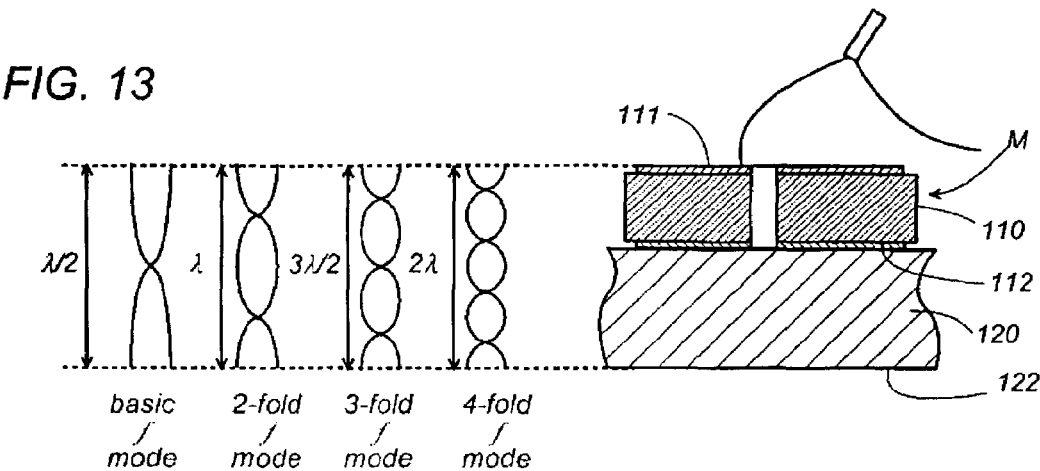
FIG. 13 is a schematic view illustrating a relation between the wavelength of the ultrasound of different frequencies and a combined vibration mass of the applicator head.

As shown in FIG. 13, the total thickness (T) of the combined vibration mass M of the piezoelectric element 110 and the horn 120 is selected to be half of wavelength ($T=\lambda/2$) of the ultrasound vibrating at a basic frequency of, for example, 3 MHz so that the combined vibration mass M can resonate also at the frequencies that are integral multiples of the basic frequency, for example, 2-fold, 3-fold, and 4-fold of the basic frequency, while forming antinodes at the skin opposing face 122 of the horn 120 and at the upper surface of the electrode 111, as schematically seen in the figure.

Figure 14:
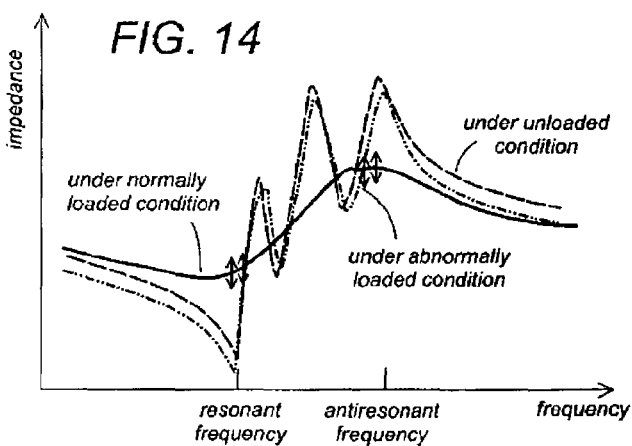
FIG. 14 is a graph illustrating, as a comparative purpose, electrically equivalent impedances of the vibration mass given under a normally loaded condition, an unloaded condition, and an abnormally loaded condition, respectively, without a structure of reducing a parasitic resonance.

In order to transmit the ultrasound power effectively to the skin at a minimum loss and also to discriminate the normally loaded condition from an abnormally loaded or the unloaded condition when actuating the combined vibration mass M around the resonant frequency, the piezoelectric element 110 is designed to have a structure that restrains vibrations at the center of the combined vibration mass M for reducing an undesired parasitic resonance which would otherwise makes the load detecting circuit 40 difficult to distinguish the normally loaded condition from the unloaded or abnormally loaded condition. That is, as shown in FIG. 14, the parasitic resonance brings about fluctuations which are superimposed on the electrically equivalent impedance curves as indicated by dotted lines with respect to varying frequency when the vibration mass M is under the unloaded condition or the abnormally loaded condition. With this result, it becomes practically difficult to distinguish the normally loaded condition from the unloaded or abnormally loaded condition on the basis of the impedance of the vibration mass M in the vicinity of the resonant or antiresonant frequencies. Consequently, it becomes hardly possible to extract the varying impedance indicating the contacting pressure of the vibration mass M within an admissible range as indicated by arrowed lines in the figure in the vicinity of the resonant or antiresonant frequencies, failing to vary the intensity of the ultrasound in accordance with the pressure at which the combination mass M is held against the user's skin, while the vibration mass M is in the normally loaded condition.

Figure 15:
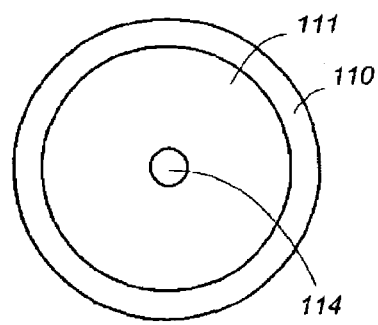
FIG. 15 is a top plan view of the vibrator element.
Figure 16:
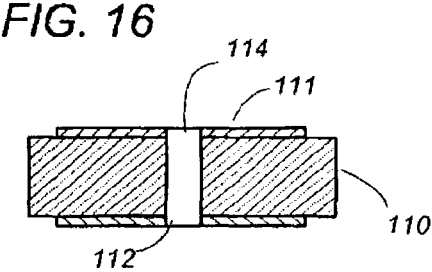
FIG. 16 is a sectional view of the vibrator element.

FIGS. 15 and 16 show one preferred structure for reducing the undesired parasitic resonance to such an extent that the load detecting circuit 40 can discriminate the normally loaded condition from the unloaded or abnormally loaded condition with reference to the electrically equivalent impedance of the combined vibration mass M. In this structure, a center opening 114 is formed to extend the center of the upper electrode 111, the piezoelectric element 110, and the lower electrode 112 for restraining the vibrations at the center of the piezoelectric element 110 and therefore the vibration mass M. With this result, the combined vibration mass M exhibits definite impedance characteristic curves in relation to the frequency under the unloaded or abnormally loaded condition, as indicated by dotted lines in FIG. 17, that can be well distinguished from the impedance curve that the vibration mass exhibits under the normally loaded condition, as indicated by solid line indicated in the same figure.

Figure 17:
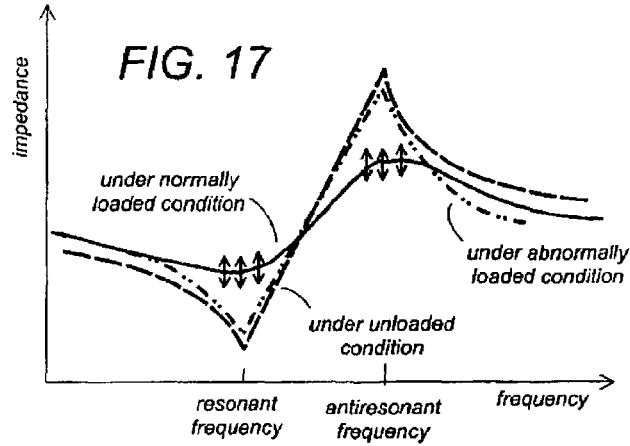
FIG. 17 is a graph illustrating the electrically equivalent impedances of the vibration mass given under the normally loaded condition, the unloaded condition, and the abnormally loaded condition, respectively, for the combined vibration mass in accordance with the embodiment of the present invention.

As apparent from FIG. 17, when subject to the unloaded or abnormally loaded condition, the vibration mass M can give the electrically equivalent impedance which are well distinctive from the impedance given under the normally loaded condition. By taking the advantage of the distinction, the load detecting circuit 40 can discriminate the abnormally loaded or unloaded condition successfully simply by monitoring the voltage reflecting the electrically equivalent impedance of the vibration mass M, as explained hereinbefore with reference to the monitoring circuit 90. In this consequence, it becomes possible to extract the impedance varying with the contacting pressure of the vibration mass M within the admissible range as indicated by arrowed lines in the figure in the vicinity of the resonant or antiresonant frequencies. Whereby, it can be made to vary the intensity of the ultrasound in accordance with the pressure at which the combination mass M is held against the user's skin, as long as the vibration mass M is in the normally loaded condition.

Figure 18:
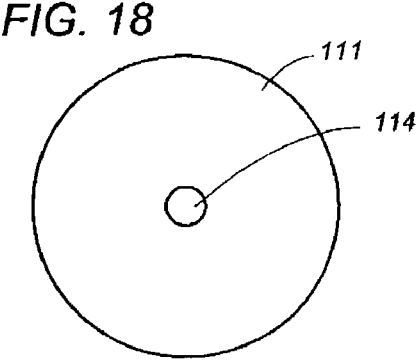
FIGS. 18 and 19 are top and sectional views of the vibrator element in accordance with a modification of the above embodiment.
Figure 19:
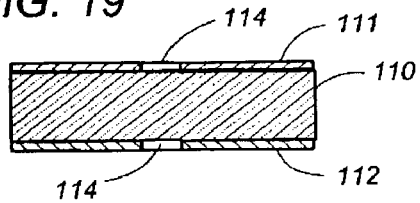

In combination with the center opening 114, at least one of the upper and lower electrodes 111 and 112 may be shaped to have a diameter smaller than that of the piezoelectric element 110 to reduce the vibrations also at the periphery of the piezoelectric element and therefore the combined vibration mass M for further reducing the parasitic resonance. The center opening 114 may be formed in at lease one of the electrodes and the piezoelectric element, for example, as shown in FIGS. 18 and 19.

Figure 20:
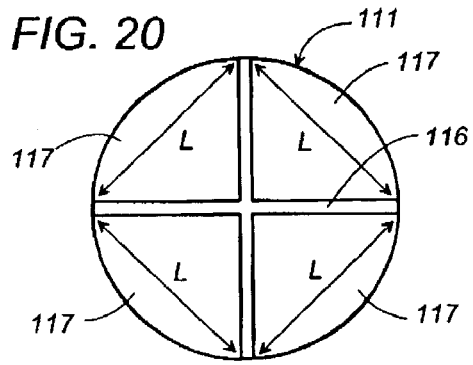
FIGS. 20 and 21 are top and sectional views of the vibrator element in accordance with another modification of the above embodiment.
Figure 21:
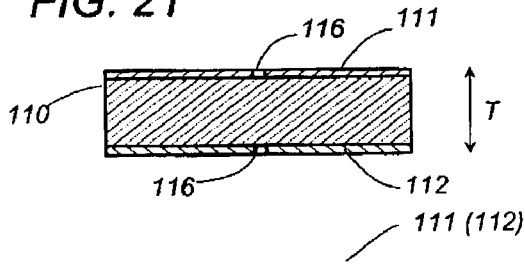

Further, as shown in FIGS. 20 and 21, the electrodes 111 and 112 may be divided by diametrically extending slits 116 into four identical segments or sectors 117. The slits extend through the center of the electrodes to leave the center and the diametrically extending band portion of the piezoelectric element uncovered, thereby restraining the vibrations at the uncovered center and the band portions and therefore reducing the undesired parasitic resonance in order to realize the impedance characteristic of FIG. 17 as well.

Figures 22, 23:
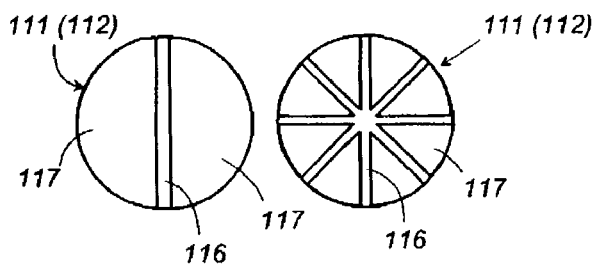
FIGS. 22 and 23 are top views illustrating further modifications of the above embodiment.

Alternatively, one or both of the electrodes 111 and 112 may be divided into two or eight segments 117, as shown in FIGS. 22 and 23 for the same purpose.

Figure 24:
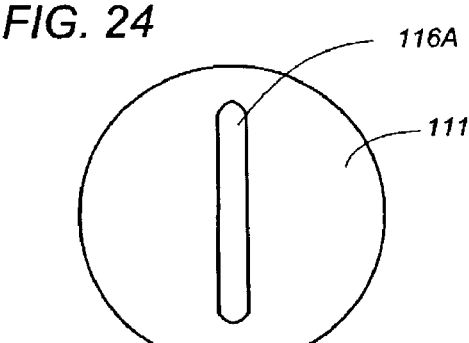
FIGS. 24 and 25 are top and sectional views of the vibrator element in accordance with a still further modification of the above embodiment.
Figure 26:
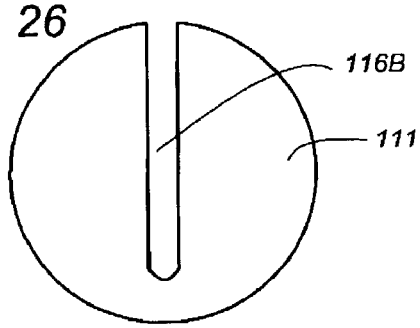
FIGS. 26 and 27 are top view illustrating further modifications of the above embodiment.
Figure 25:
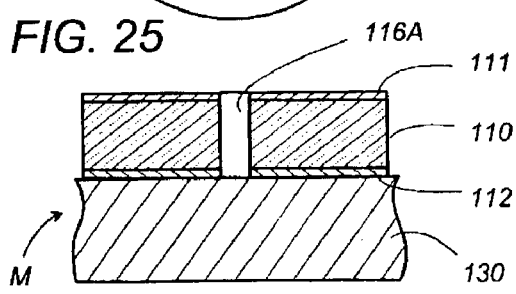
Figure 27:
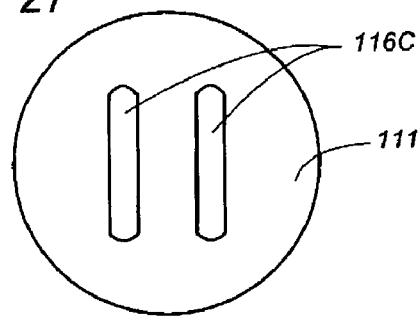

Further, it is possible to give a slit 116A with closed ends also in the piezoelectric element 110 and the electrodes 111 and 112, as shown in FIGS. 24 and 25, or to give a slit 116B open at its one end, or to give parallel slits 116C, as shown in FIGS. 26 and 27, in at least one of the electrodes and the piezoelectric element.

Figure 28:
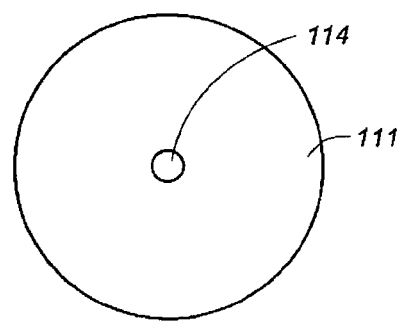
FIGS. 28 and 29 are top and sectional views of the vibrator element in accordance with a more modification of the above embodiment.
Figure 29:
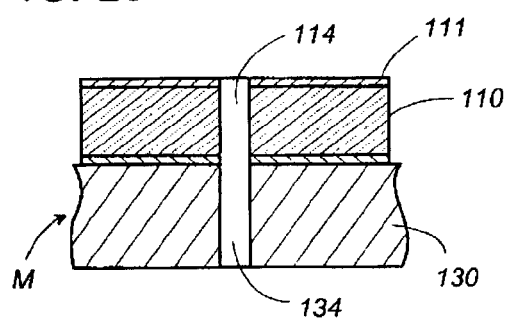
Figure 30:
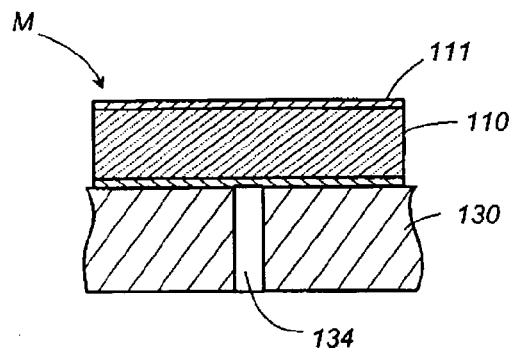
FIGS. 30 and 31 are sectional views illustrating modifications of the above embodiment.
Figure 31:
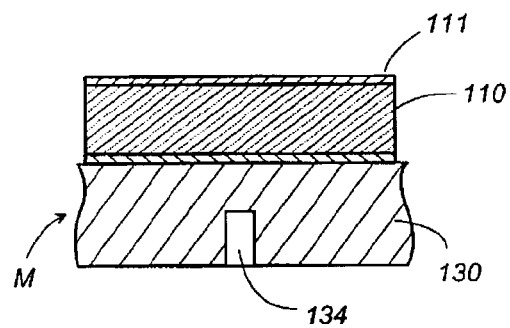

FIGS. 28 and 29 show a modification of the above embodiment in which a center hole 134 is formed in the horn 120 in alignment with the center opening 114 for further restraining the vibrations at the center of the combined vibration mass M and therefore reducing the undesired parasitic resonance to a large extent. The combination mass M may be provided only with the center hole 134 in the horn 120, as shown in FIG. 30. In this instance, the center hole 134 may be in the form of a cavity, as shown in FIG. 31.

Figure 32:
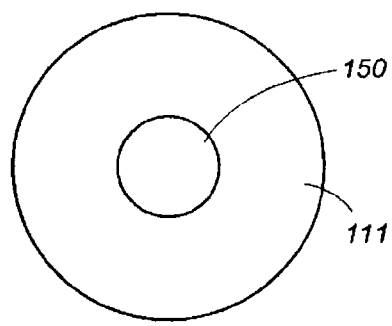
FIGS. 32 and 33 are top and sectional views of the vibrator element in accordance with a further modification of the above embodiment.
Figure 33:
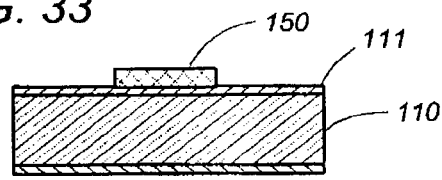
Figure 34:
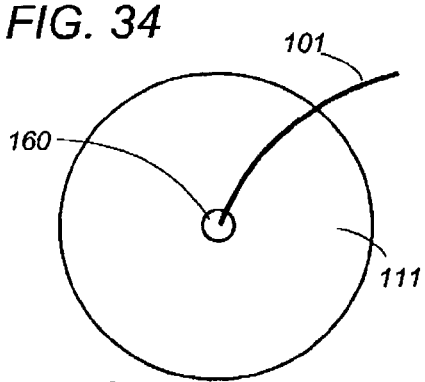
FIGS. 34 and 35 are top and sectional views of the vibrator element in accordance with a more modification of the above embodiment.
Figure 35:
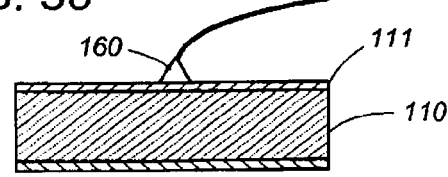

FIGS. 32 and 33 show an alternative structure in which an elastic member 150 is secured on the center of the upper electrode 111 for absorbing and therefore restraining the vibrations at the center of the piezoelectric element 110. The elastic member 150 is preferably made of a silicone rubber. Instead of providing the elastic member 150, it is equally possible to give a weight on the center of the electrode 111 for restraining the vibrations at the center of the piezoelectric element 110 and therefore reducing the undesired parasitic resonance at the center of the combined vibration mass M. The weight is given by a solder bulk 160 or land used for electrical connection of the electrode 111 to the lead wire 101 from the driver circuit 20.

It is noted in this connection that the individual structures shown with reference to FIGS. 15, 16, 18 to 35 can be suitably combined for reducing the undesired parasitic resonance. Further, where the electrodes are concerned, it is possible that one of the electrodes can be given the above structure for reducing the vibrations at the center of the vibration mass, while leaving the other electrode to cover substantially entirely the corresponding face of the piezoelectric element 110.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples 1–6

The following compositions are formed by the process described herein:

| Component | Compositions | | | | | |
|---|---|---|---|---|---|---|
| | Ex. 1 | Ex. 2 | Ex. 3 | Ex. 4 | Ex. 5 | Ex. 6 |
| Ascorbyl glucoside *1 | 2 | 2 | | 2 | 2 | 2 |
| Niacinamide *2 | 3.5 | 3.5 | 10 | 5 | 3.5 | 3.5 |
| Glycyrrhizinic acid *3 | | | 0.5 | | | |
| Acrylates/C10-30 alkyl acrylate crosspolymer *4 | 0.65 | 1 | 1 | 1 | 0.5 | 0.5 |
| Hydroxyethylcellulose *5 | 0.2 | 0.2 | 0.1 | 0.3 | | 0.5 |
| Carboxymethylcellulose *6 | | | | | 0.5 | 0.5 |
| Butylene glycol *7 | | 3 | 3 | 10 | 3 | 3 |
| Pentylene glycol *8 | 4 | | 5 | | | |
| Dimethicone/Dimethiconol *9 | 2 | 1.5 | | | | |
| Isohexadecane *10 | | | | 10 | | |
| Benzyl alcohol | | 0.2 | 0.2 | | | |
| Methylparaben | 0.15 | 0.15 | 0.15 | 0.15 | 0.15 | 0.15 |
| Disodium EDTA | 0.1 | 0.1 | 0.1 | 0.1 | 0.1 | 0.1 |
| Sodium benzoate | 0.05 | 0.05 | 0.05 | 0.05 | 0.05 | 0.05 |
| Sodium metabisulfite | 0.03 | 0.03 | 0.03 | 0.03 | 0.03 | 0.03 |
| Ethanol | 10 | | | 10 | 10 | 10 |
| Sodium hydroxide | 0.2 | 0.3 | 0.3 | 0.3 | 0.2 | 0.2 |
| Deionized Water | To make total 100% | | | | | |

Definitions of Components
*1 Ascorbyl glucoside: Ascorbic Acid 2-Glucoside available from Hayashibara
*2 Niacinamide: Niacinamide USP available from Reilly
*3 Glycyrrhizinic acid: Glycyrrhizinic acid available from Maruzen
*4 Acrylates/C10—30 alkyl acrylate crosspolymer: Pemulen TR-2 available from B. F. Goodrich Company
*5 Hydroxyethylcellulose: Natrosol Hydroxyethylcellulose available from Aqualon
*6 Carboxymethylcellulose: Aqualon Cellulose Gum available from Aqualon
*7 Butylene glycol: 1,3-Butylene Glycol available from Celanese
*8 Pentylene glycol: Hydrolite-5 available from Dragoco
*9 Dimethicone/Dimethiconol: DC-1503 available from Dow Corning
*10 Isohexadecane: Permethyl 101A from Presperse Method of Preparation The skin care compositions of Examples 1–6 can be prepared by any conventional method known in the art. Suitably, the compositions are prepared as follows:

Cellulose derivative polymer, and acrylates/C10–30 alkyl acrylate crosspolymer, as included, are added in water and mixed to dissolve. The obtained mixture is heated to at least about 70°C, and butylene glycol, pentylene glycol, Dimethicone/Dimethiconol, isohexadecane, benzyl alcohol, methylparaben, disodium EDTA, sodium metabisulfite, and sodium benzoate, as included in the composition, are added. The obtained mixture is cooled to no greater than about 40°C, and ascorbyl glucoside, niacinamide, glycyrrhizinic acid, and ethanol, as included, are added. The finally obtained mixture is neutralized with sodium hydroxide. All of the compositions have a pH of between 5 and 8.

These embodiments represented by the previous figures and examples are useful as skin care devices.

When ultrasound at a frequency of from about 3 MHz to about 10 MHz and intensity of from about 0.1 W/cm$^2$ to about 2 W/cm$^2$ is applied by the present apparatus utilizing any of the present composition of Examples 1–6 as a medium, the composition assisted in moving the device along the surface of the skin, while also effectively delivering the ultrasounds, and retaining a stable gel structure. Further, a daily usage of the device for at least 2 weeks provided significant skin lightening benefits compared to the use of the present composition without application of ultrasound.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit

The invention claimed is:

1. A device for penetrating a skin active agent to the human body via the skin by the use of an ultrasound applying apparatus which applies ultrasound to the human body via the skin, comprising:
    (1) a composition comprising:
        (a) a safe and effective amount of the skin active agent;
        (b) a viscosifying agent that provides the composition a viscosity of from about 1,000 mPas to about 1,000,000 mPas;
        (c) from about 0.1% to about 30% of a water-soluble humectant; and
        (d) an aqueous carrier;
    wherein the composition is substantially free of surfactants; and
    (2) the ultrasound applying apparatus comprising:
        (e) an application element for applying to the skin ultrasound at a frequency of from about 3 MHz to about 10 MHz and an intensity of from about 0.1 W/cm$^2$ to about 2 W/cm$^2$; and
        (f) a control element for controlling application conditions of the application element.

2. The device of claim 1 wherein the skin active agent is selected from the group consisting of ascorbic acid compounds, vitamin B3 compounds, and mixtures thereof.

3. The device of claim 1 wherein the viscosifying agent comprises a carboxylic acid/carboxylate copolymer and a cellulose derivative polymer.

4. The device of claim 3 wherein the viscosifying agent provides a viscosity of from about 3,000 mPas to about 100,000 mPas.

5. The device of claim 1 wherein the water-soluble humectant is selected from the group consisting of butylene glycol, pentylene glycol, and mixtures thereof.

6. The device of claim 1 wherein the composition comprises about 70% or greater of water.

7. The device of claim 1 wherein the composition further comprises from about 0.1% to about 15% of an oily component.

8. The device of claim 7 wherein the oily component is selected from the group consisting of hydrocarbon oils, fatty acid esters, silicone oils, and mixtures thereof.

9. The device as set forth in claim 1, wherein
said ultrasonic applying apparatus comprising:
    a housing provided with an applicator head which applies ultrasound to a user's skin; and
    a driver circuit which gives an electric pulse for actuating said applicator head to generate the ultrasound;
said applicator head comprising:
    a vibrator element generating the ultrasound, and
    a horn having a mounting face and a skin opposing face which is adapted in use to come into contact with the skin, said horn carrying said vibrator element on said mounting face to transmit said ultrasound to the skin through said skin opposing face, said vibrator element and said horn being integrated into a combined vibration mass which resonates with the electric pulse of a resonant frequency from said driver circuit to generate the ultrasound, said combination vibration mass defining said application element that gives a first electrically equivalent impedance when it is normally loaded by contact with the skin, and gives a second electrically equivalent impedance when it is unloaded,
    a load detecting circuit which is connected to monitor whether said combined vibration mass gives the first or second electrically equivalent impedance and provides a load detection signal only upon seeing said first electrically equivalent impedance,
    a control circuit which limits or stops the electric pulse when the load detection signal is not received within a predetermined time period,
    said combined vibration mass having a structure that restrains vibrations at a center portion of said combined vibration mass to reduce a parasitic resonance, thereby differentiating said first electrically equivalent impedance from said second electrically equivalent impedance for discrimination therebetween,
    said control circuit constituting a control element that receives said first electrically equivalent impedance in order to vary the intensity of the ultrasound generated at said vibrator element in accordance with the magnitude of said first electrically equivalent impedance.

10. The device as set forth in claim 9, wherein
said horn is formed as an integral part thereof with a rim which surrounds said horn and is connected to said housing,
said horn and said rim defines therebetween a restrictor which restricts the ultrasound vibrations from propagating towards said rim.

11. The ultrasound applying skin care device as set forth in claim 10 wherein
said restrictor is defined by a cavity formed at the boundary between said horn and said rim.

12. The ultrasound applying skin care device as set forth in claim 9, further including:
    a motion detecting circuit which monitors whether said combined vibration mass is moving and provides a motion detection signal when said vibration mass is so moving;
    said control circuit controlling said driver circuit to stop or limit said electric pulse when said load detection signal is not received within said predetermined time period or when said motion detection signal is not continuous over a critical time duration even in the presence of said load detection signal being detected within said time period.

13. The device as set forth in claim 9, wherein
said vibrator element comprises a piezoelectric element in the form of a circular disc having flat upper and lower end faces, and upper and lower electrodes respectively deposited on said upper and lower end faces, said electric pulse being applied across said upper and lower electrodes.

14. The device as set forth in claim 13, wherein
at least one of said upper electrode, said lower electrode, and said piezoelectric element has a center opening to restrain the vibrations at the center of said combined vibration mass.

15. The device as set forth in claim 14, wherein
at least one of said upper electrode and said electrode has a diameter smaller than that of said piezoelectric element to leave the peripheral portions of the corresponding end face of said piezoelectric element uncovered.

16. The device as set forth in claim 14, wherein
said horn has a center hole for restraining the vibrations at the center of said combined vibration mass.

17. The device as set forth in claim 13, wherein each of said upper electrode, said lower electrode, and said piezoelectric element has a center opening to restrain the vibrations at the center of said combined vibration mass.

18. The device as set forth in claim 13, wherein
at least one of said upper and lower electrodes is divided by at least one slit into a plurality of identical segments, said slit extending diametrically to leave the center and the diametrically extending band portion of said piezoelectric element uncovered.

19. The device as set forth in claim 13, wherein
at least one of said upper and lower electrodes has at least one slit that uncovers the center portion of said piezoelectric element.

20. The device as sa forth in claim 13, wherein
said horn has a center hole for restraining the vibrations at the center of said combined vibration mass.

21. The device as set forth in claim 13, wherein
said upper electrode is covered on its center with an elastic member absorbing the vibrations at the center of said combined vibration mass.

22. The device as set forth in claim 21, wherein
said elastic member comprises a silicone rubber.

23. The device as set forth in claim 13, wherein
said upper electrode of said piezoelectric element is covered on its center with a solder bulk for electrical connection of the upper electrode to a lead wire leading from said driver circuit, the solder bulk adding a weight to the center of the piezoelectric element.

24. A method of treating the skin comprising the steps of:
(1) applying to the skin a composition comprising:
 (a) a safe and effective amount of a skin active agent;
 (b) a viscosifying agent that provides the composition a viscosity of from about 1,000 mPas to about 1,000,000 mPas;
 (c) from about 0.1% to about 30% of a water-soluble humectant; and
 (d) an aqueous carrier;
wherein the composition is substantially free or surfactants; and
(2) applying ultrasound to the surface of the skin by an ultrasound applying apparatus comprising:
 (e) an application element for applying to the skin ultrasound at a frequency of from about 3 MHz to about 10 MHz and an intensity of from about 0.1 W/cm$^2$ to about 2 W/cm$^2$; and
 (f) a control element for controlling application conditions of the application element;
wherein the composition is used as a medium for applying ultrasound to the skin by the ultrasound applying apparatus.

25. The method of claim 24 wherein the treatment is for enhancing the appearance of the skin.

* * * * *

UNITED STATES PATENT AND TRADEMARK OFFICE
CERTIFICATE OF CORRECTION

PATENT NO. : 7,001,355 B2
APPLICATION NO. : 10/460911
DATED : February 21, 2006
INVENTOR(S) : Nunomura It is certified that error appears in the above-identified patent and that said Letters Patent is hereby corrected as shown below:

Column 4, Line 45    Delete "bums", Insert --burns--

Column 9, Line 63    Delete "scieroglucan", Insert --scleroglucan--

Column 27, Claim 20, Line 13    Delete "sa", Insert --set--

Signed and Sealed this

Eighth Day of August, 2006

JON W. DUDAS
*Director of the United States Patent and Trademark Office*